United States Patent [19]

Lollar et al.

[11] Patent Number: 5,364,771
[45] Date of Patent: Nov. 15, 1994

[54] HYBRID HUMAN/PORCINE FACTOR VIII

[75] Inventors: John S. Lollar, Decatur; Marschall S. Runge, Atlanta, both of Ga.

[73] Assignee: Emory University, Atlanta, Ga.

[21] Appl. No.: 864,004

[22] Filed: Apr. 7, 1992

[51] Int. Cl.$^5$ .................. C07K 13/00; C12N 15/11; C12N 15/12; A61K 37/00
[52] U.S. Cl. .................. 435/69.1; 435/172.3; 435/320.1; 514/12; 530/383; 536/23.5; 930/100
[58] Field of Search ............. 435/172.3, 69.1; 530/383; 514/12; 930/100

[56] References Cited

U.S. PATENT DOCUMENTS

| | | | |
|---|---|---|---|
| Re. 32,011 | 10/1985 | Zimmerman et al. | 260/112 |
| 4,757,006 | 7/1988 | Toole et al. | 435/70 |
| 4,965,199 | 10/1990 | Capon et al. | 435/69.6 |
| 4,970,300 | 11/1990 | Fulton et al. | 530/383 |
| 4,980,456 | 12/1990 | Scandella et al. | 530/383 |
| 5,004,803 | 4/1991 | Kaufman et al. | 530/383 |

OTHER PUBLICATIONS

Arai, M., et al., "Molecular basis of factor VIII inhibiton by human antibodies," 83 *J. Clin. Invest,* 1978–1984 (1989).

Burke, R. L., et al., "The functional domains of coagulation factor VIII:C," 261 *J. Biol. Chem.* 12574–12578 (1986).

Eaton, D., et al., "Proteolytic processing of human factor VIII, Correlation of specific cleavages by thrombin, factor Xa, and activated protein C with activation and inactivation of factor VIII coagulant activity," 25 *Biochem.* 505–512 (1986).

Eaton, D. L., et al., "Construction and characterization of an active factor VIII variant lacking the central one-third of the molecule," 25 *Biochem.* 8343–8347 (1986).

Eaton, D. L., et al., "Characterization of recombinant human factor VIII," 262 *J. of Biol. Chem.* 3285–3290 (1987).

Fass, D. N., et al., "Monoclonal antibodies to porcine factor VIII coagulant and their use in the isolation of active coagulant protein," 59 *Blood* 594–600 (1982).

Fay, P. J., et al., "The size of human factor VIII heterodimers and the effects produced by thrombin," 871 *Biochimica et Biophysica Acta* 268–278 (1986).

Fay, P. J., "Subunit structure of thrombin-activated human factor VIIIa," 952 *Biochimica et Biophysica Acta* 181–190 (1987).

Fay, P. J., "Reconstitution of human factor VIII from isolated subunits," 262 *Arch. Biochem. Biophys.* 525–531 (1988).

Fay, P. J., et al. "Topography of the human factor VIII-von Willebrand factor complex," 265 *J. Biol. Chem.* 6197–6202 (1990).

Fay, P. J., et al., "von Willebrand factor mediates protection of factor VIII from activated protein C-catalyzed inactivation," 266 *J. Biol. Chem.* 2172–2177 (1991).

(List continued on next page.)

*Primary Examiner*—Robert A. Wax
*Assistant Examiner*—Dian C. Jacobson
*Attorney, Agent, or Firm*—Kilpatrick & Cody

[57] ABSTRACT

A hybrid human/porcine coagulation factor VIII is produced by isolation and recombination of human and porcine factor VIII subunits, or by genetic engineering of the human and porcine factor VIII genes. Subunits of factor VIII that have been purified from human or porcine plasma are isolated, and hybrid human/porcine factor VIII is produced by mixing either porcine heavy chain subunits with human light chain subunits or by mixing human heavy chain subunits with porcine light chain subunits, thereby producing human light chain/porcine heavy chain and human heavy chain/porcine light chain hybrid molecules. These hybrid molecules are isolated by ion exchange chromatography. Alternatively, recombinant DNA methods are used to swap elements of porcine factor VIII for the corresponding elements of human factor VIII to produce hybrid human/porcine factor VIII.

19 Claims, 1 Drawing Sheet

OTHER PUBLICATIONS

Fay, P. J., et al., "Human factor VIII, subunit structure," 266 *J. Biol. Chem.* 1-6 (1991).

Fulcher, C. A., and T. S. Zimmerman, "Characterization of the human factor VIII procoagulant protein with a heterologous precipitating antibody," 79 *Proc. Nat'l. Acad. Sci. U.S.A.* 1648-1652 (1982).

Fulcher, C. A., et al., "Human factor VIII procoagulant protein," 76 *J. Clin. Invest.* 117-124 (1985).

Gitschier, J., et al., "Characterization of the human factor VIII gene," 312 *Nature* 326-330 (1984).

Hill-Eubanks, D. C., and P. Lollar, "von Willebrand factor is a cofactor for thrombin-catalyzed cleavage of the factor VIII light chain," 265 *J. Biol. Chem.* 17854-17858 (1990).

Kaufman, R. J., et al., "Synthesis processing, and secretion of recombinant human factor VIII expressed in mammalian cells," 263 *J. Biol. Chem.* 6352-6362 (1988).

Kaufman, R. J. et al., "Effect on von Willebrand factor coexpression on the synthesis and secretion of factor VIII in Chinese hamster ovary cells," 9 *Molec. Cell. Biol.* 1233-1242 (1989).

Koedam, J. A., et al., "The effect of von Willebrand factor on activation of factor VIII by factor Xa," 189 *Eur. J. Biochem.* 229-234 (1990).

Kohn, D. B., and P. W. Kantoff, "Potential applications of gene therapy," 29 *Transfusion* 812-820 (1989).

Leyte, A., et al., "Sulfation of $Tyr^{1680}$ of human blood coagulation factor VIII is essential for the interaction of factor VIII with von Willebrand factor," 266 *J. Biol. Chem.* 740-746 (1991).

Lollar, P., et al., "Activation of porcine factor VIII;C by thrombin and factor Xa," 24 *Biochemistry* 8056-8064 (1985).

Lollar, P. (J. S.) et al., "Association of the factor VIII light chain with von Willebrand factor," 263 *J. Biol. Chem.* 10451 (1988).

Lollar, P. (J. S.), et al., "Molecular characterization of commercial porcine factor VIII concentrate," 71 *Blood* 137-143 (1988).

Lollar, P. (J. S.), and C. G. Parker, "Subunit structure of thrombin-activated porcine factor VIII," 28 *Biochemistry* 666-674 (1989).

Lollar, P., and C. G. Parker, "pH-dependent denaturation of thrombin-activated porcine factor VIII," 265 *J. Biol. Chem.* 1688-1692 (1990).

Lollar, P., "The association of factor VIII with von Willebrand factor," 66 *Mayo Clin. Proc.* 542-534 (1991).

Lollar P., and E. T. Parker, "Structural basis for the decreased procoagulant activity of human factor VIII compared to the porcine homolog," 266 *J. Biol. Chem.* 12481-12486 (1991).

Mosesson, M. W., et al., "Structural model of porcine factor VIII and factor VIIIa molecules based on scanning transmission electron microscope (STEM) images and STEM mass analysis," 85 *J. Clin. Invest.* 1983-1990 (1990).

Naylor, J. A., et al., "Detection of three novel mutations in two haemophilia A patients by rapid screening of whole essential region of factor VIII gene," 377 *The Lancet* 635-639 (1991).

Pitman, D. D., and R. J. Kaufman, "Proteolytic requirements for thrombin activation of anti-hemophilic factor (factor VIII)," 85 *Proc. Nat'l. Acad. Sci. U.S.A.* 2429-2433 (1988).

Roberts H. R., and M. R. Jones, "Hemophilia and related conditions—Congenital deficiencies of prothrombin (factor II), factor V, and factors VII to XII," Ch. 153, 1453-1474, 1460, in *Hematology*, Williams, W. J., et al., ed., 1990.

Toole, J. J. et al., "Molecular cloning of a cDNA encoding human antihaemophilic factor," 312 *Nature* 342-347 (1984).

Toole, J. J., et al., "A large region ($\approx$95 kDa) of human factor VIII is dispensable for in vitro procoagulant activity," 83 *Proc. Nat'l. Acad. Sci. U.S.A.* 5939-5942 (1986).

Vehar, G. A., and E. W. Davie, "Preparation and properties of bovine factor VIII (antihemophilic factor)," 19 *Biochem*, 401-410 (1980).

Vehar, G. A., et al., "Structure of human factor VIII," 312 *Nature* 337-342 (1984).

Walker, F. J., et al., "Identification of the binding site for activated protein C on the light chain of factors V and VIII," 265 *J. Biol. Chem.* 1484-1489 (1990).

Ware, J., et al., "Localization of a factor VIII-inhibiting antibody epitope to a region between residues 338 and 362 of factor VIII heavy chain," 85 *Proc. Natl. Acad. Sci. USA* 3165-3169 (1988).

Wood, W. I., "Expression of active human factor VIII from recombinant DNA clones," 312 *Nature* 330-337 (1984).

HYBRID HUMAN/PORCINE FACTOR VIII

The government has rights in this invention arising from National Institutes of Health Grant No. HL 40921 that partially funded the research leading to this invention.

BACKGROUND OF THE INVENTION

This invention relates generally to a hybrid human/porcine factor VIII and methods of preparation and use thereof.

Blood clotting begins when platelets adhere to the cut wall of an injured blood vessel at a lesion site. Subsequently, in a cascade of enzymatically regulated reactions, soluble fibrinogen molecules are converted by the enzyme thrombin to insoluble strands of fibrin that hold the platelets together in a thrombus. At each step in the cascade, a protein precursor is converted to a protease that cleaves the next protein precursor in the series. Cofactors are required at most of the steps. In its active form, the protein factor VIII is a cofactor that is required for the activation of factor X by the protease, activated factor IX.

Factor VIII or antihemophilic factor was noticed in plasma and named in the 1930s. In the 1940s, a deficiency in factor VIII was associated with the clotting disorder hemophilia A. Factor VIII was found to be X-linked and was hypothesized to be a protein. Work involving bovine, human, and porcine plasma identified factor VIII as a protein in the 1980s, though its definitive cellular source remains uncertain.

Precisely how factor VIII functions in blood coagulation is unknown. It is known that factor VIII is activated to factor VIIIa proteolytically by thrombin or factor Xa. In combination with calcium and phospholipid, factor VIIIa makes factor IXa a more efficient activator of factor X by an unknown mechanism.

People deficient in factor VIII or having antibodies against factor VIII who are not treated with factor VIII suffer uncontrolled internal bleeding that may cause a range of serious symptoms, from inflammatory reactions in joints to early death. Severe hemophiliacs, who number about 10,000 in the United States, can be treated with infusion of factor VIII, which will restore the blood's normal clotting ability if administered with sufficient frequency and concentration. The classic definition of factor VIII, in fact, is that substance present in normal blood plasma that corrects the clotting defect in plasma derived from individuals with hemophilia A.

Several preparations of human plasma-derived factor VIII of varying degrees of purity are available commercially for the treatment of hemophilia A. These include a partially-purified factor VIII derived from the pooled blood of many donors that is heat- and detergent-treated for viruses but contains a significant level of antigenic proteins; a monoclonal antibody-purified factor VIII that has lower levels of antigenic impurities and viral contamination; and recombinant human factor VIII, clinical trials for which are underway. Additionally, a preparation of partially-purified porcine factor VIII is available to treat patients with inhibitors to human factor VIII, i.e., those who have circulating antibody molecules that bind and neutralize human factor VIII.

Hemophiliacs require daily replacement of factor VIII to prevent the deforming hemophilic arthropathy that occurs after many years of recurrent hemorrhages into the joints. However, supplies of factor VIII concentrates have never been plentiful enough for treating hemophiliacs adequately because of problems in commercial production and therapeutic use. For example, the commonly used plasma-derived is difficult to isolate and purify, is immunogenic, and requires treatment to remove the risk of infectivity from AIDS and hepatitis viruses. Recombinant human factor VIII may lessen the latter two problems. Porcine factor VIII may also present an alternative, since human factor VIII is unstable at physiologic concentrations and pH, is present in blood at an extremely low concentration (0.2 $\mu$g/ml plasma), and its specific clotting activity is low, compared with porcine factor VIII.

Since many inhibitors of human factor VIII react less strongly with porcine factor VIII, porcine factor VIII is currently used to correct factor VIII deficiency in patients under conditions in which they do not respond to infusions of human factor VIII. A limitation of porcine factor VIII is the development of inhibitory antibodies to it after one or more infusions.

The problems associated with the commonly used, commercially available, plasma-derived factor VIII have stimulated significant interest in the development of a better factor VIII product. There is a need for a more potent factor VIII molecule so that more units of clotting activity can be delivered per molecule; a factor VIII molecule that is stable at a selected pH and physiologic concentration; a factor VIII molecule that is less apt to produce inhibitory antibodies; and a factor VIII molecule that evades immune detection in patients who have already acquired antibodies to human factor VIII.

It is therefore an object of the present invention to provide a factor VIII that corrects hemophilia in a patient deficient in factor VIII or having inhibitors of human factor VIII.

It is a further object of the present invention to provide methods for treatment of hemophiliacs.

It is another object of the present invention to provide a factor VIII with an increased efficacy in factor VIII clotting assays.

It is still another object of the present invention to provide a factor VIII that is stable at a selected pH and physiologic concentration.

SUMMARY OF THE INVENTION

A hybrid human/porcine coagulation factor VIII is produced by isolation and recombination of human and porcine factor VIII subunits or by genetic engineering of the human and porcine factor VIII genes.

In the preferred embodiment, subunits of factor VIII are isolated and purified from human or porcine plasma, and hybrid human/porcine factor VIII is produced either by mixture of porcine heavy chain subunits with human light chain subunits or by mixture of human heavy chain subunits with porcine light chain subunits, thereby producing human light chain/porcine heavy chain and human heavy chain/porcine light chain hybrid molecules. These hybrid molecules are isolated by ion exchange chromatography.

Alternatively, recombinant DNA methods are used to swap elements of porcine factor VIII for the corresponding elements of human factor VIII, also resulting in hybrid human/porcine factor VIII molecules.

Methods for preparing highly purified hybrid human/porcine factor VIII are described having the steps of: (a) isolation of subunits of plasma-derived human factor VIII and subunits of plasma-derived porcine factor VIII, followed by reconstitution of coagulant activity by mixture of human and porcine subunits, followed by isolation of hybrid human/porcine factor VIII by ion exchange chromatography; (b) construction of domains of porcine factor VIII by recombinant DNA technology, followed by swapping of domains of porcine and human factor VIII; or (c) creation of hybrid human/porcine factor VIII by replacement of specific amino acid residues of human factor VIII with the homologous porcine factor VIII amino acid residues by site-directed mutagenesis.

The resulting hybrid human/porcine factor VIII has specific activity greater than human factor VIII and equal to or slightly higher than porcine factor VIII.

DETAILED DESCRIPTION OF THE INVENTION

Definitions

Figure 1:
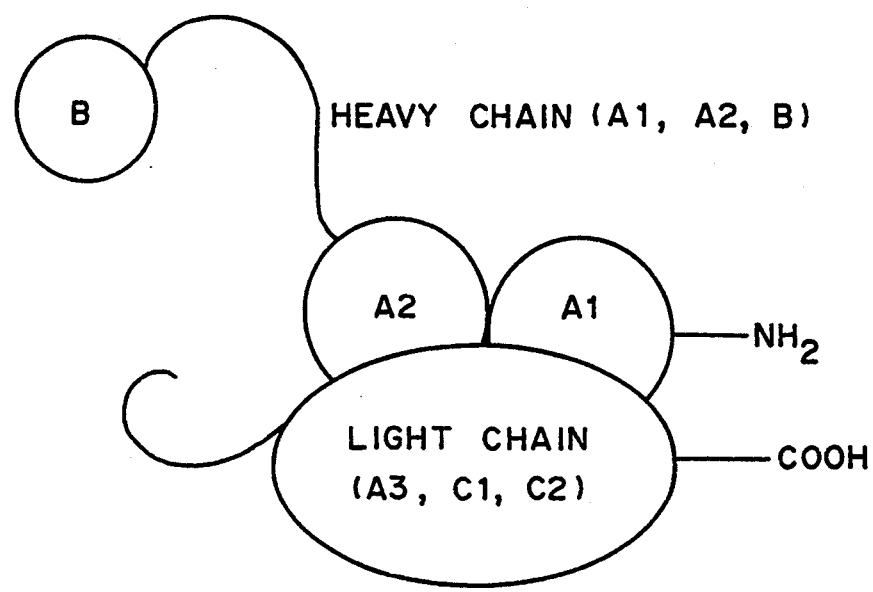
FIG. 1 (Prior Art) is a diagrammatic representation of factor VIII molecule showing the subunits (heavy and light chains) and the domains.

As used herein, "hybrid human/porcine factor VIII" denotes a functional factor VIII protein molecule with sequence derived from human and porcine factor VIII. This hybrid human/porcine factor VIII has a specific activity equal to or greater than that of porcine factor VIII and has activity in a human factor VIII assay. In some embodiments, this hybrid human/porcine factor VIII is not cross-reactive with all human factor VIII antibodies.

"Specific activity," as used herein, refers to the activity that will correct the coagulation defect of human factor VIII deficient plasma. Specific activity is measured in units of clotting activity per milligram total factor VIII protein in a standard assay in which the clotting time of human factor VIII deficient plasma is compared to that of normal human plasma. One unit of factor VIII activity is the activity present in one milliliter of normal human plasma. In the assay, the shorter the time for clot formation, the greater the activity of the factor VIII being assayed.

A "hybrid factor VIII" or "hybrid protein," as used herein is a factor VIII protein in which the amino acid sequence is derived in part from human and in part from porcine origin. This hybrid factor VIII can be made (1) by substitution of isolated, plasma-derived porcine or human subunits (heavy or light chains) for corresponding human or porcine subunits; (2) by substitution of human or porcine domains (A1, A2, A3, B, C1, and C2) for corresponding porcine or human domains; (3) by substitution of parts of human or porcine domains for parts of porcine or human domains; or (4) by changing one or more amino acid residue(s) in human factor VIII to the residue(s) in the corresponding porcine sequence. A fusion protein is the product of a hybrid gene in which the coding sequence for one protein is extensively altered, for example, by fusing part of it to the coding sequence for a second protein from a different gene to produce a hybrid gene that encodes the fusion protein. As used herein, a fusion protein is a subset of the hybrid protein described in this application.

"Factor VIII deficiency," as used herein, includes deficiency in clotting activity caused by production of a defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII protein it encodes.

"Subunits" of human or porcine factor VIII, as used herein, are the heavy and light chains of the protein. The heavy chain of factor VIII contains three "domains," A1, A2, and B. The light chain of factor VIII also contains three "domains," A3, C1, and C2.

General Description of Methods

Hybrid human/porcine factor VIII molecules that have greater activity in a standard clotting assay when compared to highly—purified human factor VIII can be constructed as follows.

Four types of hybrid human/porcine factor VIII and the methods for preparing them are disclosed herein: those obtained (1) (a) by substituting a porcine subunit (i.e., heavy chain or light chain) for the corresponding human subunit; (b) by substituting a porcine domain (i.e., A1, A2, A3, B, C1, and C2) for the corresponding human domain; and (c) by substituting part of a porcine domain for the corresponding fragment of the human domain; and (2) by changing one or more amino acid residue(s) in human factor VIII to the residue(s) in the corresponding porcine sequence. The hybrid molecule may contain a greater percentage of human than porcine sequence or vice versa, depending on the origin of the various regions, as described in more detail below.

It is shown below that hybrid human/porcine factor VIII consisting of porcine heavy chain/human light chain and corresponding to the first type of hybrid listed above has greater specific coagulant activity in a standard clotting assay as compared to human factor VIII. The hybrid human/porcine factor VIII can be useful in treating patients with inhibitors, since these inhibitors can react less well with hybrid human/porcine factor VIII than with either human or porcine factor VIII.

Hybrid human/porcine factor VIII proteins listed above under group (1) are made by isolation of subunits of plasma-derived factor VIII, followed by reconstitution and purification. Hybrid human/porcine factor VIII proteins described under group (2) above are made by recombinant DNA methods.

Preparation of hybrid human/porcine factor VIII molecules from isolated human and porcine factor VIII subunits by reconstitution:

Hybrid human/porcine factor VIII molecules are prepared and isolated, and their procoagulant activity is characterized. One method, modified from procedures reported by Fay, P. J., et al., 265 J. Biol. Chem. 6197 (1990), the teachings of which are incorporated herein; and Lollar, J. S., et al., 263 J. Biol. Chem. 10451 (1988), the teachings of which are incorporated herein, involves the isolation of subunits (heavy and light chains) of human and porcine factor VIII, followed by recombination of human heavy chain and porcine light chain or by recombination of human light chain and porcine heavy chain.

Isolation of individual subunits from both species involves dissociation of the light chain/heavy chain dimer by chelation of calcium with ethylenediaminetetraacetic acid (EDTA), followed by Mono S ™ HPLC (Pharmacia-LKB, Piscataway, N.J.). Hybrid human/porcine factor VIII molecules are reconstituted from isolated subunits in the presence of calcium. Hybrid human light chain/porcine heavy chain or porcine light chain/human heavy chain factor VIII is isolated from unreacted heavy chains by Mono S ™ HPLC by procedures for the isolation of porcine factor VIII, as described by Lollar, J. S., et al., 71 Blood 137-143 (1988), the teachings of which are incorporated herein.

These methods, described in detail in the examples below, result in hybrid human light chain/porcine heavy chain molecules with greater than six times the procoagulant activity of human factor VIII.

Preparation of human/porcine factor VIII molecules by recombinant engineering of the sequences encoding human and porcine factor VIII subunits:

The human factor VIII gene was isolated and expressed in mammalian cells, as reported by Toole, J. J., et al., 312 Nature 342-347 (1984) (Genetics Institute); Gitschier, J., et al, 312 Nature 326-330 (1984) (Genentech); Wood, W. I., et al., 312 Nature 330-337 (1984) (Genentech); Vehar, G. A., et al., 312 Nature 337-342 (1984) (Genentech)), the teachings of each of which are incorporated herein, and the amino acid sequence was deduced from cDNA. U.S. Pat. No. 4,965,199 to Capon et al., discloses a recombinant DNA method for producing factor VIII in mammalian host cells and purification of human factor VIII. Factor VIII expression in CHO (Chinese hamster ovary) cells and BHKC (baby hamster kidney cells) has been reported.

The cDNA sequence encoding human factor VIII and predicted amino acid sequence are shown as SEQ ID No: 3 and SEQ ID No: 4, respectively.

Recombinant hybrid human/porcine factor VIII is prepared starting with human cDNA (Biogen, Inc.) encoding the factor VIII sequence corresponding to domains A1-A2-A3-C1-C2. This cDNA lacks the entire B domain and corresponds to residues 1-740 and 1649-2332 of single chain human factor VIII (SEQ ID NO: 3), according to the numbering system of Wood et al., 312 Nature 330-337 (1984), the teachings of which are incorporated herein. The B domain is deleted, since it does not appear to be necessary for biological function.

Porcine factor VIII has been isolated and purified from plasma (Fass, D. N., et al., 59 Blood 594 (1982). The amino acid sequence of the B and part of the A2 domains of porcine factor VIII, as reported by Toole, J. J., et al., 83 Proc. Nat'l. Acad. Sci. U.S.A. 5939-5942 (1986), the teachings of which are incorporated herein, and the corresponding genomic DNA sequence are shown as SEQ ID NO: 6 and SEQ ID NO: 5, respectively. The coding region in the nucleotide sequence begins at position 675 (GGT CTC TGG . . .) (SEQ ID NO: 5), which corresponds to amino acids (Gly-Leu-Trp) (SEQ ID NO: 6), the NH2 terminal amino acids.

Both porcine and human factor VIII are isolated from plasma as a two subunit protein. FIG. 1 (prior art) illustrates diagrammatically the subunit structure of the molecule. The subunits, known as the heavy chain and light chain, are held together by a non-covalent bond that requires calcium or other divalent metal ions. The heavy chain of factor VIII contains three domains, A1, A2, and B, which are linked covalently. The light chain of factor VIII also contains three domains designated A3, C1, and C2. The B domain has no known function and can be removed from the molecule proteolytically or by recombinant DNA technology methods without significant alteration in any measurable parameter of factor VIII. Human recombinant factor VIII has a similar structure and function to plasma-derived factor VIII, though it is not glycosylated unless expressed in mammalian cells.

Both human and porcine activated factor VIII (factor VIIIa) have three subunits due to cleavage of the heavy chain between the A1 and A2 domains. This structure is designated A1/A2/A3-C1-C2. Human factor VIIIa is not stable under the conditions that stabilize porcine factor VIIIa. This is because of the weaker association of the A2 subunit of human factor VIIIa. Dissociation of the A2 subunit of human and porcine factor VIIIa is associated with loss of activity.

Since the nucleotide sequence of the porcine B domain is known, full length hybrids can be constructed. Individual domains of porcine factor VIII cDNA can be cloned and substituted for the corresponding human domains by established mutagenesis techniques. These factor VIII cDNA molecules can be cloned into expression vectors for ultimate expression of active hybrid human/porcine factor VIII protein molecules.

The complete A2 domain of porcine factor VIII, homologous to residues 372-740 in mature human factor VIII (SEQ ID NO: 3), was sequenced and the amino acid sequence was predicted. These sequences are shown as SEQ ID NO: 1 and SEQ ID NO: 2, respectively.

Pharmaceutical Compositions

Pharmaceutical compositions containing hybrid human/porcine factor VIII, alone or in combination with appropriate pharmaceutical stabilization compounds, delivery vehicles, and/or carrier vehicles, are prepared according to known methods as described in *Remington's Pharmaceutical Sciences* by E. W. Martin, the teachings of which are incorporated herein.

In one preferred embodiment, the preferred carriers or delivery vehicles for intravenous infusion are physiological saline or phosphate buffered saline.

In another preferred embodiment, suitable stabilization compounds, delivery vehicles, and carrier vehicles include but are not limited to other human or porcine proteins such as albumin.

Phospholipid vesicles or liposomal suspensions are also preferred as pharmaceutically acceptable carriers or delivery vehicles. These can be prepared according to methods known to those skilled in the art and can contain, for example, phosphatidylserine/-phosphatidylcholine or other compositions of phospholipids or detergents that together impart a negative charge to the surface, since factor VIII binds to negatively charged phospholipid membranes. Liposomes may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the hybrid human/porcine factor VIII is then introduced into the container. The container is then swirled by hand to free lipid material from the sides of the container and to disperse lipid aggregates, thereby forming the liposomal suspension.

The hybrid human/porcine factor VIII can be combined with other suitable stabilization compounds, delivery vehicles, and/or carrier vehicles, including vitamin K dependent clotting factors, and von Willebrand factor (vWf) or a fragment of vWf that contains the factor VIII binding site, and polysaccharides such as sucrose.

Hybrid human/porcine factor VIII can also be delivered by gene therapy in the same way that human factor VIII can be delivered, using delivery means such as retroviral vectors. This method consists of incorporation of factor VIII cDNA into human cells that are transplanted directly into a factor VIII deficient patient or that are placed in an implantable device, permeable to the factor VIII molecules but impermeable to cells, that is then transplanted. The preferred method will be retroviral-mediated gene transfer. In this method, an exogenous gene (e.g., a factor VIII cDNA) is cloned into the genome of a modified retrovirus. The gene is inserted into the genome of the host cell by viral machinery where it will be expressed by the cell. The retroviral vector is modified so that it will not produce virus, preventing viral infection of the host. The general principles for this type of therapy are known to those skilled in the art and have been reviewed in the literature (e.g., Kohn, D. B., and P. W. Kantoff, 29 Transfusion 812-820, 1989).

Hybrid human/porcine factor VIII can be stored bound to vWf to increase the half-life and shelf-life of the hybrid molecule. Additionally, lyophilization of factor VIII can improve the yields of active molecules in the presence of vWf. Current methods for storage of human and porcine factor VIII used by commercial suppliers can be employed for storage of hybrid human/porcine factor VIII. These methods include: (1) lyophilization of factor VIII in a partially-purified state (as a factor VIII "concentrate" that is infused without further purification); (2) immunoaffinity-purification of factor VIII by the Zimmerman method and lyophilization in the presence of albumin, which stabilizes the factor VIII; (3) lyophilization of recombinant factor VIII in the presence of albumin.

Additionally, hybrid human/porcine factor VIII has been indefinitely stable at 4° C. in 0.6M NaCl, 20 mM MES, and 5mM $CaCl_2$ at pH 6.0 and also can be stored frozen in these buffers and thawed with minimal loss of activity.

Method of Treatment

Hybrid human/porcine factor VIII is used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. The active materials are preferably administered intravenously. Additionally, hybrid human/porcine factor VIII can be administered by transplant of cells genetically engineered to produce the hybrid or by implantation of a device containing such cells, as described above.

In a preferred embodiment, pharmaceutical compositions of hybrid human/porcine factor VIII alone or in combination with stabilizers, delivery vehicles, and/or carriers are infused into patients intravenously according to the same procedure that is used for infusion of human or porcine factor VIII.

The treatment dosages of hybrid human/porcine factor VIII composition that must be administered to a patient in need of such treatment will vary depending on the severity of the factor VIII deficiency. Generally, dosage level is adjusted in frequency, duration, and units in keeping with the severity and duration of each patient's bleeding episode. Accordingly, the hybrid human/porcine factor VIII is included in the pharmaceutically acceptable carrier, delivery vehicle, or stabilizer in an amount sufficient to deliver to a patient a therapeutically effective amount of the hybrid to stop bleeding, as measured by standard clotting assays.

Usually, the desired plasma factor VIII level to be achieved in the patient through administration of the hybrid human/porcine factor VIII is in the range of 30-100% of normal. In a preferred mode of administration of the hybrid human/porcine factor VIII, the composition is given intravenously at a preferred dosage in the range from about 20 to 50 units/kg body weight; the interval frequency is in the range from about 8 to 24 hours (in severely affected hemophiliacs); and the duration of treatment in days is in the range from 1 to 10 days or until the bleeding episode is resolved See, e.g., Roberts, H. R., and M. R. Jones, "Hemophilia and Related Conditions—Congenital Deficiencies of Prothrombin (Factor II, Factor V, and Factors VII to XII)," Ch. 153, 1453-1474, 1460, in Hematology, Williams, W. J., et al., ed., 1990. Patients with inhibitors may require more hybrid human/porcine factor VIII, or patients may require less hybrid human/porcine factor VIII because of its higher specific activity than human factor VIII. As in treatment with human or porcine factor VIII, the amount of factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

Treatment can take the form of a single intravenous administration of the composition or periodic or continuous administration over an extended period of time, as required. Alternatively, hybrid human/porcine factor VIII can be administered subcutaneously or orally with liposomes in one or several doses at varying intervals of time.

The hybrid human/porcine factor VIII molecule and the methods for isolation, characterization, making, and using it generally described above will be further understood with reference to the following non-limiting examples.

EXAMPLE 1:

Assay of porcine factor VIII and hybrid human/porcine factor VIII

Porcine factor VIII has more coagulant activity than human factor VIII, based on specific activity of the molecule. These results are shown in Table II in Example 4. This conclusion is based on the use of appropriate standard curves that allow human and porcine factor VIII to be fairly compared. Coagulation assays are based on the ability of factor VIII to shorten the clotting time of plasma derived from a patient with hemophilia A. Two types of assays were employed: the one-stage and the two-stage assay.

In the one-stage assay, 0.1 ml hemophilia A plasma (George King Biomedical, Inc.) was incubated with 0.1 ml activated partial thromboplastin reagent (APTT) (Organon Teknika) and 0.01 ml sample or standard, consisting of diluted, citrated normal human plasma, for 5 min at 37° C. in a water bath. Incubation was followed by addition of 0.1 ml 20 mM $CaCl_2$, and the time for development of a fibrin clot was determined by visual inspection.

A unit of factor VIII is defined as the amount present in 1 ml of citrated normal human plasma. With human plasma as the standard, porcine and human factor VIII activity were compared directly. Dilutions of the plasma standard or purified proteins were made into 0.15M NaCl, 1, 0.02M HEPES, pH 7.4. The standard curve was constructed based on 3 or 4 dilutions of plasma, the highest dilution being 1/50, and on $\log_{10}$ clotting time plotted against $\log_{10}$ plasma concentration, which results in a linear plot. The units of factor VIII in an unknown sample were determined by interpolation from the standard curve.

The one-stage assay relies on endogenous activation of factor VIII by activators formed in the hemophilia A plasma, whereas the two-stage assay measures the procoagulant activity of preactivated factor VIII. In the two-stage assay, samples containing factor VIII that had been reacted with thrombin were added to a mixture of activated partial thromboplastin and human hemophilia A plasma that had been preincubated for 5 min at 37° C. The resulting clotting times were then converted to units/ml, based on the same human standard curve described above. The relative activity in the two-stage assay was higher than in the one-stage assay because the factor VIII had been preactivated.

EXAMPLE 2:

Characterization of the functional difference between human and porcine factor VIII.

The isolation of porcine and human plasma-derived factor VIII and human recombinant factor VIII have been described in the literature. Fulcher, C. A., and T. S. Zimmerman, 79 *Proc. Nat'l. Acad. Sci. U.S.A.* 1648–1652 (1982); Toole, J. J., et al., 312 Nature 342–347 (1984) (Genetics Institute); Gitschier, J., et al., 312 Nature 326–330 (1984) (Genentech); Wood, W. I., et al., 312 Nature 330–337 (1984) (Genentech); Vehar, G. A., et al., 312 Nature 337–342 (1984) (Genentech); Fass, D. N., et al., 59 Blood 594 (1982); Toole, J. J., et al., 83 *Proc. Nat'l. Acad. Sci. U.S.A.* 5939–5942 (1986). This can be accomplished in several ways. All these preparations are similar in subunit composition, although this is the first description of the functional difference between human and porcine factor VIII, not noted previously in part due to the lack of use of a common standard by which to compare them.

For comparison of human recombinant and porcine factor VIII, preparations of highly-purified human recombinant factor VIII (Cutter Laboratories, Berkeley, Calif.) and porcine factor VIII (immunopurified as described in Fass, D. N., et al., 59 Blood 594 (1982)) were subjected to high-pressure liquid chromatography (HPLC) over a Mono Q TM (Pharmacia-LKB, Piscataway, N.J.) anion-exchange column (Pharmacia, Inc.). The purposes of the Mono Q TM HPLC step were elimination of minor impurities and exchange of human and porcine factor VIII into a common buffer for comparative purposes. Vials containing 1000–2000 units of factor VIII were reconstituted with 5 ml H2O. Hepes (2M at pH 7.4) was then added to a final concentration of 0.02M. Factor VIII was applied to a Mono Q TM HR 5/5 column equilibrated in 0.15M NaCl, 0.02M Hepes, 5 mM CaCl2, at pH 7.4 (Buffer A plus 0.15M NaCl); washed with 10 ml Buffer A+0.15M NaCl; and eluted with a 20 ml linear gradient, 0.15M to 0.90M NaCl in Buffer A at a flow rate of 1 ml/min.

For comparison of human factor VIII (derived from plasma and purified by Mono Q TM HPLC) and porcine factor VIII, immunoaffinity-purified, plasma-derived porcine factor VIII was diluted 1:4 with 0.04M Hepes, 5 mM CaCl2, 0.01% Tween-80, at pH 7.4, and subjected to Mono Q TM HPLC under the same conditions described in the previous paragraph for human factor VIII. These procedures for the isolation of human and porcine factor VIII are standard for those skilled in the art.

Column fractions were assayed for factor VIII activity by a one-stage coagulation assay. The average results of the assays, expressed in units of activity per $A_{280}$ of material, are given in Table I, and indicate that porcine factor VIII has at least six times greater activity than human factor VIII when the one-stage assay is used.

TABLE I

COMPARISON OF HUMAN AND PORCINE FACTOR VIII COAGULANT ACTIVITY

|  | Activity (U/$A_{280}$) |
|---|---|
| Porcine | 21,300 |
| Human plasma-derived | 3,600 |
| Human recombinant | 2,400 |

EXAMPLE 3:

Comparison of the stability of human and porcine factor VIIIa

The results of the one-stage assay for factor VIII reflect activation of factor VIII to factor VIIIa in the sample and possibly loss of formed factor VIIIa activity. A direct comparison of the stability of human and porcine factor VIII was made. Samples from Mono Q TM HPLC were diluted to the same concentration and buffer composition and reacted with thrombin. At various times, samples were removed for two-stage coagulation assay. Typically, peak activity (at 2 min) was 10-fold greater for porcine than human factor VIIIa, and the activities of both porcine and human factor VIIIa subsequently decreased, with human factor VIIIa activity decreasing more rapidly.

Generally, attempts to isolate stable human factor VIIIa are not successful even when conditions that produce stable porcine factor VIIIa are used. To demonstrate this, Mono Q TM HPLC-purified human factor VIII was activated with thrombin and subjected to Mono S TM cation-exchange (Pharmacia, Inc.) HPLC under conditions that produce stable porcine factor VIIIa (Lollar, J. S., and Parker, C. G., 28 Biochemistry 666, 1989, the teachings of which are incorporated herein).

Human factor VIII, 43 μg/ml (0.2 μM) in 0.2M NaCl, 0.01M Hepes, 2.5 mM CaCl2, at pH 7.4, in 10 ml total volume, was reacted with thrombin (0.036 μM) for 10 min, at which time FPR-CH2Cl D-phenyl-prolyl-arginyl-chloromethyl ketone was added to a concentration of 0.2 μM for irreversible inactivation of thrombin. The mixture then was diluted 1:1 with 40 mM 2-(N-morpholino)ethane sulfonic acid (MES), 5 mM CaCl2, at pH 6.0, and loaded at 2 ml/min onto a Mono S TM HR 5/5 HPLC column equilibrated in 5 mM MES, 5 mM CaCl2, at pH 6.0 (Buffer B) plus 0.1M NaCl. Factor VIIIa was eluted without column washing with a 20 ml gradient from 0.1M NaCl to 0.9M NaCl in Buffer B at 1 ml/min.

The fraction with coagulant activity in the two-stage assay eluted as a single peak under these conditions. The specific activity of the peak fraction was approximately 7,500 U/$A_{280}$. Sodium dodecyl sulfate-polyacrylamide gel electrophoresis (SDS-PAGE) of the Mono S ™ factor VIIIa peak, followed by silver staining of the protein, revealed two bands corresponding to a heterodimeric (A3-C1-C2/A1) derivative of factor VIII. Although the A2 fragment was not identified by silver staining under these conditions because of its low concentration, it was identified as a trace constituent by $^{125}$I-labeling.

In contrast to the results with human factor VIII, porcine factor VIIIa isolated by Mono S ™ HPLC under the same conditions had a specific activity $1.6 \times 10^6$ U/$A_{280}$. Analysis of porcine factor VIIIa by SDS-PAGE revealed 3 fragments corresponding A1, A2, and A3- C1-C2 subunits, demonstrating that porcine factor VIIIa possesses three subunits.

The results of Mono S ™ HPLC of human thrombin-activated factor VIII preparations at pH 6.0 indicate that human factor VIIIa is labile under conditions that yield stable porcine factor VIIIa. However, although trace amounts of A2 fragment were identified in the peak fraction, determination of whether the coagulant activity resulted from small amounts of heterotrimeric factor VIIIa or from heterodimeric factor VIIIa that has a low specific activity was not possible from this method alone.

A way to isolate human factor VIIIa before it loses its A2 subunit is desirable to resolve this question. To this end, isolation was accomplished in a procedure that involves reduction of the pH of the Mono S ™ buffers to pH 5. Mono Q ™-purified human factor VIII (0.5 mg) was diluted with H$_2$O to give a final composition of 0.25 mg/ml (1 µM) factor VIII in 0.25M NaCl, 0.01M Hepes, 2.5 mM CaCl$_2$, 0.005% Tween-80, at pH 7.4 (total volume 7.0 ml). Thrombin was added to a final concentration of 0.072 µM and allowed to react for 3 min. Thrombin was then inactivated with FPR-CH$_2$Cl (0.2 µM). The mixture then was diluted 1:1 with 40 mM sodium acetate, 5 mM CaCl$_2$, 0.01% Tween-80, at pH 5.0, and loaded at 2 ml/min onto a Mono Sυ HR 5/5 HPLC column equilibrated in 0.01M sodium acetate, 5 mM CaCl$_2$, 0.01% Tween-80, at pH 5.0, plus 0.1M NaCl. Factor VIIIa was eluted without column washing with a 20 ml gradient from 0.1M NaCl to 1.0M NaCl in the same buffer at 1 ml/min. This resulted in recovery of coagulant activity in a peak that contained detectable amounts of the A2 fragment as shown by SDS-PAGE and silver staining. The specific activity of the peak fraction was ten-fold greater than that recovered at pH 6.0 (75,000 U/$A_{280}$ vs. 7,500 U/$A_{280}$). However, in contrast to porcine factor VIIIa isolated at pH 6.0, which is indefinitely stable at 4° C., human factor VIIIa activity decreased steadily over a period of several hours after elution from Mono S ™. Additionally, the specific activity of factor VIIIa purified at pH 5.0 and assayed immediately is only 5% that of porcine factor VIIIa, indicating that substantial dissociation occurred prior to assay.

These results demonstrate that both human and porcine factor VIIIa are composed of three subunits (A1, A2, and A3-C1-C2). Dissociation of the A2 subunit is responsible for the loss of activity of both human and porcine factor VIIIa under certain conditions, such as physiological ionic strength, pH, and concentration. The relative stability of porcine factor VIIIa under certain conditions is because of stronger association of the A2 subunit.

EXAMPLE 4:

Preparation of hybrid human/porcine factor VIII.

Porcine factor VIII light chains and factor VIII heavy chains were isolated as follows. A 0.5M solution of EDTA at pH 7.4 was added to Mono Q ™-purified porcine factor VIII to a final concentration of 0.05M and was allowed to stand at room temperature for 18–24 h. An equal volume of 10 mM histidine-Cl, 10 mM EDTA, 0.02% v/v Tween 80, at pH 6.0 (Buffer B), was added, and the solution was applied at 1 ml/min to a Mono S ™ HR 5/5 column previously equilibrated in Buffer A plus 0.25M NaCl. Factor VIII heavy chains did not bind the resin, as judged by SDS-PAGE. Factor VIII light chain was eluted with a linear, 20 ml, 0.1–0.7M NaCl gradient in Buffer A at 1 ml/min and was homogeneous by SDS-PAGE. Factor VIII heavy chains were isolated by mono Q HPLC in the following way. Factor VIII heavy chains do not adsorb to mono S during the purification of factor VIII light chains. The fall-through material that contained factor VIII heavy chains was adjusted to pH 7.2 by addition of 0.5M Hepes buffer, pH 7.4, and applied to a mono Q HR5/5 HPLC column equilibrated in 0.1M NaCl, 0.02M Hepes, 0.01% Tween-80, pH 7.4. The column was washed with 10 mL of this buffer, and factor VIII heavy chains were eluted with a 20 mL 0.1–1.0M NaCl gradient in this buffer. Human light chains and heavy chains were isolated in the same manner.

Human and porcine light and heavy chains were reconstituted according to the following steps. Ten 1 human or porcine factor VIII light chain, 100 g/ml, was mixed in 1M NaCl, 0.02M Hepes, 5 mM CaCl$_2$, 0.01% Tween-80, pH 7.4, with (1) 25 1 heterologous heavy chain, 60 g/ml, in the same buffer; (2) 10 10.02M Hepes, 0.01% Tween-80, pH 7.4; (3) 5 10.6M CaCl$_2$, for 14 hr at room temperature. The mixture was diluted ¼ with 0.02M MES, 0.01% Tween-80, 5 mM CaCl$_2$, pH 6, and applied to Mono S Hr5/5 equilibrated in 0.1M NaCl, 0.02M MES, 0.01% Tween-80, 5mM CaCl$_2$, pH 6.0. A 20 ml gradient was run from 0.1–1.0M NaCl in the same buffer at 1 ml/min, and 0.5 ml fractions were collected. Absorbance was read at 280 nm of fractions, and fractions were assayed with absorbance for factor VIII activity by the one-stage clotting assay. Heavy chains were present in excess, because free light chain (not associated with heavy chain) also binds Mono S ™; excess heavy chains ensure that free light chains are not part of the preparation. Reconstitution experiments followed by Mono S ™ HPLC purification were performed with all four possible combinations of chains: human light chain/human heavy chain, human light chain/porcine heavy chain, porcine light chain/porcine heavy chain, porcine light chain/human heavy chain.

Table II shows that human light chain/porcine heavy chain factor VIII has activity comparable to native porcine factor VIII (Table I), indicating that structural elements in the porcine heavy chain are responsible for the increased coagulant activity of porcine factor VIII compared to human factor VIII.

TABLE II

COMPARISON OF HYBRID HUMAN/PORCINE FACTOR VIII COAGULANT ACTIVITY WITH HUMAN AND PORCINE FACTOR VIII

| | Activity (U/$A_{280}$) |
| --- | --- |
| Porcine light chain/porcine heavy chain | 30,600 |
| Human light chain/porcine heavy chain | 44,100 |

TABLE II-continued
COMPARISON OF HYBRID HUMAN/PORCINE FACTOR VIII COAGULANT ACTIVITY WITH HUMAN AND PORCINE FACTOR VIII

| | Activity (U/A$_{280}$) |
|---|---|
| Porcine light chain/human heavy chain | 1,100 |
| Human light chain/human heavy chain | 1,000 |

EXAMPLE 5:

Isolation and sequencing of the A2 domain of porcine factor VIII.

Only the B domain and part of the A2 domain of porcine factor VIII have been sequenced previously (Toole, J. J., et al., 83 *Proc. Nat'l. Acad. Sci. U.S.A.* 5939–5942 (1986)) (SEQ ID NO; 5). The genomic DNA sequence of the porcine factor VIII B domain and the cDNA sequence for the entire porcine factor VIII A2 domain are disclosed herein (SEQ ID NO: 2 and SEQ ID NO: 1, respectively).

The porcine factor VIII A2 domain was cloned by reverse transcription of porcine spleen total RNA and PCR amplification; degenerate primers based on the known human factor VIII cDNA sequence and an exact porcine primer based on a part of the porcine factor VIII sequence were used. A 1 kb PCR product was isolated and amplified by insertion into a Bluescript TM (Stratagene) phagemid vector.

The porcine A2 domain was completely sequenced by dideoxy sequencing. The sequence is as described in SEQ ID NO: 1.

EXAMPLE 6:

Preparation of recombinant hybrid human/porcine factor VIII

The sequence of human factor VIII has been described in the literature (Toole, J. J., et al., 312 Nature 342–347 (1984) (Genetics Institute); Gitschier, J., et al., 312 Nature 326–330 (1984) (Genentech); Wood, W. I., et al., 312 Nature 330–337 (1984) (Genentech); Vehar, G. A., et al., 312 Nature 337–342 (1984) (Genentech)). The sequence is as described in SEQ ID NO: 3.

Making recombinant hybrid human/porcine factor VIII requires that a region of human factor VIII cDNA (Biogen Corp.) be removed and the homologous porcine cDNA sequence inserted. Subsequently, the hybrid cDNA is expressed in an appropriate expression system. In these experiments, for example, the entire cDNA sequence corresponding to the A2 domain of human factor VIII is removed by oligonucleotide-mediated mutagenesis, a method commonly known to those skilled in the art (see, e.g., Sambrook, J., E. F. Fritsch, and T. Maniatis, *Molecular Cloning: A Laboratory Manual*, Chapter 15, Cold Spring Harbor Press, Cold Spring Harbor, 1989).

The steps were as follows: *E. coli* CJ236 cells were transformed with Bluescript TM phage containing the human factor VIII cDNA insert. Single-stranded Bluescript TM /human factor VIII circular DNA was produced with M13K07 helper phage and then purified by standard methods (Sambrook, J., E. F. Fritsch, and T. Maniatis, *Molecular Cloning: A Laboratory Manual*, Chapter 4, Cold Spring Harbor Press, Cold Spring Harbor, 1989). A mutagenic oligonucleotide was synthesized corresponding to the 3' end of the A1 domain and the 5=end of the A3 domain:

5'
CCTTCCTTTATCCAAATACGTAGAT-
CAAGAGGAAATTGAC 3'.

Additionally this oligonucleotide provides a SnaB1 restriction site that can be used to insert the porcine A2 domain. On hybridization of this oligonucleotide to single strand Bluescript TM /human factor VIII, the region between the A1 and A3 domains, i.e, the A2 domain, was "looped out." The resulting heteroduplex was extended to circular, double-stranded DNA by use of T7 polymerase, ligated, and used to transform *E. coli* XL1-blue TM (Stratagene) cells. Transformants were screened by isolation of phagemid DNA from several colonies, Xho1 digestion, and examination of the size of phagemid DNA by agarose gel electrophoresis. Three clones were identified that were shorter than human factor VIII/Bluescript TM by 1 kb, as expected for deletion of the 1 kb A2 domain. The results were confirmed by sequencing across the boundaries of the A1 and A3 domains.

The porcine A2 domain has been inserted between the A1 and A3 domains of the human factor VIII cDNA by (1) PCR amplification of the porcine A2 domain; (2) gel purification of the PCR product (agarose gel electrophoresis of the PCR product producing a band visualized by ethidium bromide staining, followed by excision of the band and purification of the DNA to remove agarose and other contaminants); and (3) ligation by using T4 DNA ligase of the porcine A2 cDNA to the human A2-domainless cDNA linearized by using the SnaB1 restriction site. The primers used for PCR amplification of the porcine A2 were as follows:

5' primer: 5'
GTAGCGTTTGCCAAGAAGCACC-
CTAAGACG 3'

3' primer: 5'
GAAGACTAGTACGACT-
TATTTCTCTGGGTTCAATGAC 3'.

The 3' primer contains nucleotides corresponding to residues 736–740 of the porcine factor VIII protein sequence (at the C-terminus of the A2 domain) (SEQ ID NO: 2), and residues 1649–1656 of the human factor VIII sequence (at the N-terminus of the A3 domain) (SEQ ID NO: 4). The A3 sequence residues were included because the looping out procedure removed these residues. The ligated product was used to transform XL1-Blue cells, producing several colonies that contained the desired porcine A2 insert when analyzed by PCR. The product contains an unwanted thymine at the A1–A2 junction as a result of the PCR amplification of the porcine A2 domain. This single base can be looped out by use of the mutagenic oligonucleotide

5'
CCTTTATCCAAATACGTAGCGTTTG-
CCAAGAAG 3', and the product can be cloned exactly as described above (Under Example 6, paragraph 3) for the production of human A2-deficient cDNA.

Cloning of the porcine A1, A3, C1, and C2 domains is feasible with the same strategy that was used for cloning the porcine A2 domain. Fragments of these domains can be cloned by the looping out mutagenesis technique. Excision of the corresponding domains in human factor VIII and any fragments thereof, including single amino acid eliminations, is feasible by looping out mutagenesis as described above. All possible domain replacements, fragments of domain replacements, or single amino acid residue replacements are possible by this approach.

The biological activity of recombinant hybrid human/porcine factor VIII can be evaluated initially by use of a COS-cell mammalian transient expression system. Hybrid human/porcine cDNA can be transfected into COS cells, and supernatants can be analyzed for factor VIII activity by use of one-stage and two-stage coagulation assays as described above in Example 1. Additionally, factor VIII activity can be measured by use of a chromogenic substrate assay, which is more sensitive and allows analysis of larger numbers of samples. This assay has been described (Lollar, P., G. J. Knutson, and D. N. Fass, 24 Biochemistry 8056-8064, 1985). Similar assays are standard in the assay of factor VIII activity (Wood, W. I., et al., 312 Nature 330-337, 1984; Toole, J. J., et al., 312 Nature 342-347, 1984). Expression of recombinant factor VIII in COS cells is a standard procedure (Toole, J. J., et al., 312 Nature 342-347, 1984; Pittman, D. D., and R. J. Kaufman, 85 Proc. Nat'l. Acad. Sci. USA 2429-2433, 1988). The human factor VIII cDNA used as starting material for the recombiant molecules described herein has been expressed in COS cells yielding a product with biological activity. This material will be used a standard to compare hybrid human/porcine factor VIII molecules. The activity in the assays is converted to a specific activity for proper comparison of the hybrid molecules. For this, a measurement of the mass of factor VIII produced by the cells is necessary and can be done by immunoassay with purified human and/or porcine factor VIII as standards. Immunoassays for factor VIII are routine for those skilled in the art (See, e.g., Lollar, P., et al., 71 Blood 137-143, 1988).

Sequences of human and porcine factor VIII likely to be involved as epitopes (i.e., as recognition sites for inhibitory antibodies) can be determined through use of commercially available predictive computer programs, such as MacVector (IBI Corp., New Haven, Conn.). Sequences of porcine factor VIII that are not antigenic compared to corresponding (homologous) antigenic human sequences will be identified, and substitutions will be made to insert porcine sequences and delete human sequences according to standard recombinant DNA methods. It is already known that porcine factor VIII reacts less than human factor VIII with some inhibitory antibodies; this provides a basis for current therapy for patients with inhibitors. After the recombinant hybrids are made, they will be tested in vitro for reactivity with the Bethesda inhibitor assay. Those constructs that are less reactive than native human factor VIII and native porcine factor VIII will be candidates for replacement therapy.

Although only preferred embodiments are specifically illustrated and described herein, it will be appreciated that many modifications and variations of the present invention are possible in light of the above teachings and within purview of the appended claims without departing from the spirit and intended scope of the invention.

We claim:

1. A purified hybrid factor VIII molecule comprising porcine and human amino acid sequences, wherein the molecule has procoagulant activity in an in vitro coagulation assay and wherein the molecule is selected from the group consisting of
    a molecule consisting essentially of a human factor VIII in which the porcine A2 domain is substituted for the homologous human factor VIII A2 domain;
    a molecule consisting essentially of a porcine factor VIII in which the human A2 domain is substituted for the homologous porcine factor VIII A2 domain;
    a molecule consisting essentially of a human light chain factor VIII subunit and a porcine heavy chain factor VIII subunit; and
    a molecule consisting essentially of a porcine light chain factor VIII subunit and a human heavy chain factor VIII subunit.

2. The molecule of claim 1, wherein the molecule has a specific activity greater than 20,000 U/A$_{280}$ protein in aqueous solution when human plasma is used as the standard in a one-stage coagulation assay.

3. The molecule of claim 1, wherein the hybrid human/procine factor VIII is combined with a pharmaceutically acceptable carrier.

4. The molecular of claim 3, wherein the carrier is selected from the group consisting of stabilizing agents and delivery vehicles.

5. The molecule of claim 4, wherein the stabilizing agents are selected from the group consisting of proteins and polysaccharides.

6. The molecule of claim 3, further comprising clotting factors selected from the group consisting of von Willebrand factor, vitamin K dependent clotting factors, and coagulant tissue factor.

7. The molecule of claim 4, wherein the delivery vehicles are liposomes.

8. A method of preparing puirified hybrid human/porcine factor VIII comprising
    combining primary amino acid sequence derived from procine factor VIII with primary amino acid sequence derived from human factor VIII to form a hybrid factor VIII molecule having procoagulant activity in an in vitro coagulation assay, wherein the molecule is selected from the group consisting of
    a molecule consisting essentially of a human light chain factor VIII subunit and a procine heavy chain factor VIII subunit; and
    a molecule consisting essentially of a porcine light chain factor VIII subunit and a human heavy chain factor VIII subunit.

9. The method of claim 8, wherein the hybrid human/porcine factor VIII molecule is formed by isolating and purifying heavy and light chain subunits of human factor VIII and porcine factor VIII, then mixing the human and porcine subunits to form the hybrid human/porcine factor VIII.

10. The method of claim 9, wherein the human and porcine factor VIII subunits are isolated from human and porcine plasma.

11. A method of preparing purified hybrid human/porcine factor VIII comprising
    expressing recombinant DNA encoding domains in the light chain and heavy chain subunits of porcine and human factor VIII, further comprising
    substituting A2 domains of porcine and human factor VIII, to form the purified hybrid human/porcine factor VIII having primary amino acid sequence derived from porcine factor VIII and primary amino acid sequence derived from human factor VIII and having procoagulant activity in an in vitro coagulation assay.

12. The method of claim 9, wherein the hybrid human/porcine factor VIII molecule is formed by mixing human light chain factor VIII subunits and porcine heavy chain factor VIII subunits.

13. The method of claim 9, wherein the hybrid human/porcine factor VIII molecule is formed by mixing porcine light chain factor VIII subunits and human heavy chain factor VIII subunits.

14. The molecule of claim 1, wherein the molecule consists essentially of a human factor VIII in which the porcine A2 domain is substituted for the homologous human factor VIII A2 domain.

15. The molecule of claim 1, wherein the molecule consists essentially of a porcine factor VIII in which the human A2 domain is substituted for the homologous porcine factor VIII A2 domain.

16. The molecule of claim 1, wherein the molecule consists essentially of a human light chain factor VIII subunit and a porcine heavy chain factor VIII subunit.

17. The molecule of claim 1, wherein the molecule consists essentially of a porcine light chain factor VIII subunit and a human heavy chain factor VIII subunit.

18. The method of claim 11, wherein the hybrid human/porcine factor VIII molecule is formed by substituting the porcine A2 domain in human factor VIII.

19. The method of claim 11, wherein the hybrid human/porcine factor VIII molecule is formed by substituting the human A2 domain in porcine factor VIII.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 1130 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Porcine
( F ) TISSUE TYPE: Blood ( x i ) SEQUENCE DESCRIPTION: SEQ ID NO:1:

```
TAAGCACCCT AAGACGTGGG TGCACTACAT CTCTGCAGAG GAGGAGGACT GGGACTACGC    60
CCCCGCGGTC CCCAGCCCCA GTGACAGAAG TTATAAAAGT CTCTACTTGA ACAGTGGTCC   120
TCAGCGAATT GGTAGGAAAT ACAAAAAAGC TCGATTCGTC GCTTACACGG ATGTAACATT   180
TAAGACTCGT AAAGCTATTC CGTATGAATC AGGAATCCTG GGACCTTTAC TTTATGGAGA   240
AGTTGGAGAC ACACTTTTGA TTATATTTAA GAATAAAGCG AGCCGACCAT ATAACATCTA   300
CCCTCATGGA ATCACTGATG TCAGCGCTTT GCACCCAGGG AGACTTCTAA AAGGTTGGAA   360
```

| ACATTTGAAA | GACATGCCAA | TTCTGCCAGG | AGAGACTTTC | AAGTATAAAT | GGACAGTGAC | 420 |
| CTGTGGAAGAT | GGGCCAACCA | AGTCCGATCC | TCGGTGCCTG | ACCCGCTACT | ACTCGAGCTC | 480 |
| CATTAATCTA | GAGAAAGATC | TGGCTTCGGG | ACTCATTGGC | CCTCTCCTCA | TCTGCTACAA | 540 |
| AGAATCTGTA | GACCAAAGAG | GAAACCAGAT | GATGTCAGAC | AAGAGAAACG | TCATCCTGTT | 600 |
| TTCTGTATTC | GATGAGAATC | AAAGCTGGTA | CCTCGCAGAG | AATATTCAGC | GCTTCCTCCC | 660 |
| CAATCCGGAT | GGATTACAGC | CCCAGGATCC | AGAGTTCCAA | GCTTCTAACA | TCATGCACAG | 720 |
| CATCAATGGC | TATGTTTTTG | ATAGCTTGCA | GCTGTCGGTT | TGTTTGCACG | AGGTGGCATA | 780 |
| CTGGTACATT | CTAAGTGTTG | GAGCACAGAC | GGACTTCCTC | TCCGTCTTCT | TCTCTGGCTA | 840 |
| CACCTTCAAA | CACAAAATGG | TCTATGAAGA | CACACTCACC | CTGTTCCCCT | TCTCAGGAGA | 900 |
| AACGGTCTTC | ATGTCAATGG | AAAACCCAGG | TCTCTGGGTC | CTAGGGTGCC | ACAACTCAGA | 960 |
| CTTGCGGAAC | AGAGGGATGA | CAGCCTTACT | GAAGGTGTAT | AGTTGTGACA | GGGACATTGG | 1020 |
| TGATTATTAT | GACAACACTT | ATGAAGATAT | TCCAGGCTTC | TTGCTGAGTG | GAAAGAATGT | 1080 |
| CATTGAACCC | AGAAGCTTTG | CCCAGAATTC | AAGACCCCCT | AGTGCGAGCA | | 1130 |

( 2 ) INFORMATION FOR SEQ ID NO:2:

( i ) SEQUENCE CHARACTERISTICS:
        ( A ) LENGTH: 367 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Porcine
        ( F ) TISSUE TYPE: Spleen ( x i ) SEQUENCE DESCRIPTION: SEQ ID NO:2:

```
Val Ala Lys Lys His Pro Lys Thr Trp Val His Tyr Ile Ser Ala Glu
 1               5                  10                  15

Glu Glu Asp Trp Asp Tyr Ala Pro Ala Val Pro Ser Pro Ser Asp Arg
                20                  25                  30

Ser Tyr Lys Ser Leu Tyr Leu Asn Ser Gly Pro Gln Arg Ile Gly Arg
            35                  40                  45

Lys Tyr Lys Lys Ala Arg Phe Val Ala Tyr Thr Asp Val Thr Phe Lys
        50                  55                  60

Thr Arg Lys Ala Ile Pro Tyr Glu Ser Gly Ile Leu Gly Pro Leu Leu
65                  70                  75                  80

Tyr Gly Glu Val Gly Asp Thr Leu Leu Ile Ile Phe Lys Asn Lys Ala
                85                  90                  95

Ser Arg Pro Tyr Asn Ile Tyr Pro His Gly Ile Thr Asp Val Ser Ala
            100                 105                 110

Leu His Pro Gly Arg Leu Leu Lys Gly Trp Lys His Leu Lys Asp Met
        115                 120                 125

Pro Ile Leu Pro Gly Glu Thr Phe Lys Tyr Lys Trp Thr Val Thr Val
    130                 135                 140

Glu Asp Gly Pro Thr Lys Ser Asp Pro Arg Cys Leu Thr Arg Tyr Tyr
145                 150                 155                 160

Ser Ser Ser Ile Asn Leu Glu Lys Asp Leu Ala Ser Gly Leu Ile Gly
                165                 170                 175
```

| | | | | | | | | | | | | | | |
|---|---|---|---|---|---|---|---|---|---|---|---|---|---|---|
|Pro|Leu|Leu|Ile<br>180|Cys|Tyr|Lys|Glu|Ser<br>185|Val|Asp|Gln|Arg|Gly<br>190|Asn|Gln|
|Met|Met|Ser<br>195|Asp|Lys|Arg|Asn|Val<br>200|Ile|Leu|Phe|Ser|Val<br>205|Phe|Asp|Glu|
|Asn|Gln<br>210|Ser|Trp|Tyr|Leu|Ala<br>215|Glu|Asn|Ile|Gln|Arg<br>220|Phe|Leu|Pro|Asn|
|Pro<br>225|Asp|Gly|Leu|Gln|Pro<br>230|Gln|Asp|Pro|Glu|Phe<br>235|Gln|Ala|Ser|Asn|Ile<br>240|
|Met|His|Ser|Ile|Asn<br>245|Gly|Tyr|Val|Phe|Asp<br>250|Ser|Leu|Gln|Leu|Ser<br>255|Val|
|Cys|Leu|His|Glu<br>260|Val|Ala|Tyr|Trp|Tyr<br>265|Ile|Leu|Ser|Val|Gly<br>270|Ala|Gln|
|Thr|Asp|Phe<br>275|Leu|Ser|Val|Phe|Phe<br>280|Ser|Gly|Tyr|Thr|Phe<br>285|Lys|His|Lys|
|Met|Val<br>290|Tyr|Glu|Asp|Thr|Leu<br>295|Thr|Leu|Phe|Pro|Phe<br>300|Ser|Gly|Glu|Thr|
|Val<br>305|Phe|Met|Ser|Met|Glu<br>310|Asn|Pro|Gly|Leu|Trp<br>315|Val|Leu|Gly|Cys|His<br>320|
|Asn|Ser|Asp|Leu|Arg<br>325|Asn|Arg|Gly|Met|Thr<br>330|Ala|Leu|Leu|Lys|Val<br>335|Tyr|
|Ser|Cys|Asp|Arg<br>340|Asp|Ile|Gly|Asp|Tyr<br>345|Tyr|Asp|Asn|Thr|Tyr<br>350|Glu|Asp|
|Ile|Pro|Gly<br>355|Phe|Leu|Leu|Ser|Gly<br>360|Lys|Asn|Val|Ile|Glu<br>365|Pro|Arg| |

( 2 ) INFORMATION FOR SEQ ID NO:3:

( i ) SEQUENCE CHARACTERISTICS:
        ( A ) LENGTH: 9009 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapien
        ( F ) TISSUE TYPE: Liver ( i x ) FEATURE:
        ( A ) NAME/KEY: miscfeature (Domain Structure)
        ( B ) LOCATION: 5001 . . . 7053
        ( D ) OTHER INFORMATION: /note="Equivalent to the A3-C1-C2
            domain"

( i x ) FEATURE:
        ( A ) NAME/KEY: miscfeature (Domain Structure)
        ( B ) LOCATION: 1 . . . 2277
        ( D ) OTHER INFORMATION: /note="Equivalent to the A1-A2
            domain"

( x i ) SEQUENCE DESCRIPTION: SEQ ID NO:3:

```
CAGTGGGTAA GTTCCTTAAA TGCTCTGCAA AGAAATTGGG ACTTTTCATT AAATCAGAAA        60

TTTTACTTTT TTCCCCTCCT GGGAGCTAAA GATATTTTAG AGAAGAATTA ACCTTTTGCT       120

TCTCCAGTTG AACATTTGTA GCAATAAGTC ATGCAAATAG AGCTCTCCAC CTGCTTCTTT       180

CTGTGCCTTT TGCGATTCTG CTTTAGTGCC ACCAGAAGAT ACTACCTGGG TGCAGTGGAA       240

CTGTCATGGG ACTATATGCA AAGTGATCTC GGTGAGCTGC CTGTGGACGC AAGATTTCCT       300

CCTAGAGTGC CAAAATCTTT TCCATTCAAC ACCTCAGTCG TGTACAAAAA GACTCTGTTT       360
```

```
GTAGAATTCA CGGTTCACCT TTTCAACATC GCTAAGCCAA GGCCACCCTG GATGGGTCTG    420
CTAGGTCCTA CCATCCAGGC TGAGGTTTAT GATACAGTGG TCATTACACT TAAGAACATG    480
GCTTCCCATC CTGTCAGTCT TCATGCTGTT GGTGTATCCT ACTGGAAAGC TTCTGAGGGA    540
GCTGAATATG ATGATCAGAC CAGTCAAAGG GAGAAAGAAG ATGATAAAGT CTTCCCTGGT    600
GGAAGCCATA CATATGTCTG GCAGGTCCTG AAAGAGAATG GTCCAATGGC CTCTGACCCA    660
CTGTGCCTTA CCTACTCATA TCTTTCTCAT GTGGACCTGG TAAAAGACTT GAATTCAGGC    720
CTCATTGGAG CCCTACTAGT ATGTAGAGAA GGGAGTCTGG CCAAGGAAAA GACACAGACC    780
TTGCACAAAT TATACTACT TTTTGCTGTA TTTGATGAAG GGAAAAGTTG GCACTCAGAA    840
ACAAAGAACT CCTTGATGCA GGATAGGGAT GCTGCATCTG CTCGGGCCTG GCCTAAAATG    900
CACACAGTCA ATGGTTATGT AAACAGGTCT CTGCCAGGTC TGATTGGATG CCACAGGAAA    960
TCAGTCTATT GGCATGTGAT TGGAATGGGC ACCACTCCTG AAGTGCACTC AATATTCCTC   1020
GAAGGTCACA CATTTCTTGT GAGGAACCAT CGCCAGGCGT CCTTGGAAAT CTCGCCAATA   1080
ACTTTCCTTA CTGCTCAAAC ACTCTTGATG GACCTTGGAC AGTTTCTACT GTTTTGTCAT   1140
ATCTCTTCCC ACCAACATGA TGGCATGGAA GCTTATGTCA AGTAGACAG CTGTCCAGAG    1200
GAACCCCAAC TACGAATGAA AATAATGAA GAAGCGGAAG ACTATGATGA TGATCTTACT    1260
GATTCTGAAA TGGATGTGGT CAGGTTTGAT GATGACAACT CTCCTTCCTT TATCCAAATT   1320
CGCTCAGTTG CCAAGAAGCA TCCTAAAACT TGGGTACATT ACATTGCTGC TGAAGAGGAG   1380
GACTGGGACT ATGCTCCCTT AGTCCTCGCC CCCGATGACA GAAGTTATAA AAGTCAATAT   1440
TTGAACAATG GCCCTCAGCG GATTGGTAGG AAGTACAAAA AAGTCCGATT TATGGCATAC   1500
ACAGATGAAA CCTTTAAGAC TCGTGAAGCT ATTCAGCATG AATCAGGAAT CTTGGGACCT   1560
TTACTTTATG GGGAAGTTGG AGACACACTG TTGATTATAT TTAAGAATCA AGCAAGCAGA   1620
CCATATAACA TCTACCCTCA CGGAATCACT GATGTCCGTC CTTTGTATTC AAGGAGATTA   1680
CCAAAAGGTG TAAAACATTT GAAGGATTTT CCAATTCTGC CAGGAGAAAT ATTCAAATAT   1740
AAATGGACAG TGACTGTAGA AGATGGGCCA ACTAAATCAG ATCCTCGGTG CCTGACCCGC   1800
TATTACTCTA GTTTCGTTAA TATGGAGAGA GATCTAGCTT CAGGACTCAT TGGCCCTCTC   1860
CTCATCTGCT ACAAAGAATC TGTAGATCAA AGAGGAAACC AGATAATGTC AGACAAGAGG   1920
AATGTCATCC TGTTTTCTGT ATTTGATGAG AACCGAAGCT GGTACCTCAC AGAGAATATA   1980
CAACGCTTTC TCCCCAATCC AGCTGGAGTG CAGCTTGAGG ATCCAGAGTT CCAAGCCTCC   2040
AACATCATGC ACAGCATCAA TGGCTATGTT TTTGATAGTT TGCAGTTGTC AGTTTGTTTG   2100
CATGAGGTGG CATACTGGTA CATTCTAAGC ATTGGAGCAC AGACTGACTT CCTTTCTGTC   2160
TTCTTCTCTG GATATACCTT CAAACACAAA ATGGTCTATG AAGACACACT CACCCTATTC   2220
CCATTCTCAG GAGAAACTGT CTTCATGTCG ATGGAAAACC CAGGTCTATG GATTCTGGGG   2280
TGCCACAACT CAGACTTTCG GAACAGAGGC ATGACCGCCT TACTGAAGGT TTCTAGTTGT   2340
GACAAGAACA CTGGTGATTA TTACGAGGAC AGTTATGAAG ATATTTCAGC ATACTTGCTG   2400
AGTAAAAACA ATGCCATTGA ACCAAGAAGC TTCTCCCAGA ATTCAAGACA CCCTAGCACT   2460
AGGCAAAAGC AATTTAATGC CACCACAATT CCAGAAAATG ACATAGAGAA GACTGACCCT   2520
TGGTTTGCAC ACAGAACACC TATGCCTAAA ATACAAAATG TCTCCTCTAG TGATTTGTTG   2580
ATGCTCTTGC GACAGAGTCC TACTCCACAT GGGCTATCCT TATCTGATCT CCAAGAAGCC   2640
AAATATGAGA CTTTTTCTGA TGATCCATCA CCTGGAGCAA TAGACAGTAA TAACAGCCTG   2700
TCTGAAATGA CACACTTCAG GCCACAGCTC CATCACAGTG GGACATGGT ATTTACCCCT    2760
GAGTCAGGCC TCCAATTAAG ATTAAATGAG AAACTGGGGA CAACTGCAGC AACAGAGTTG   2820
```

```
AAGAAACTTG ATTTCAAAGT TTCTAGTACA TCAATAATC  TGATTTCAAC AATTCCATCA    2880
GACAATTTGG CAGCAGGTAC TGATAATACA AGTTCCTTAG GACCCCCAAG TATGCCAGTT    2940
CATTATGATA GTCAATTAGA TACCACTCTA TTTGGCAAAA AGTCATCTCC CCTTACTGAG    3000
TCTGGTGGAC CTCTGAGCTT GAGTGAAGAA ATAATGATT  CAAAGTTGTT AGAATCAGGT    3060
TTAATGAATA GCCAAGAAAG TTCATGGGGA AAAAATGTAT CGTCAACAGA GAGTGGTAGG    3120
TTATTTAAAG GGAAAAGAGC TCATGGACCT GCTTGTTGA  CTAAAGATAA TGCCTTATTC    3180
AAAGTTAGCA TCTCTTTGTT AAAGACAAAC AAAACTTCCA ATAATTCAGC AACTAATAGA    3240
AAGACTCACA TTGATGGCCC ATCATTATTA ATTGAGAATA GTCCATCAGT CTGGCAAAAT    3300
ATATTAGAAA GTGACACTGA GTTTAAAAAA GTGACACCTT TGATTCATGA CAGAATGCTT    3360
ATGGACAAAA ATGCTACAGC TTTGAGGCTA AATCATATGT CAAATAAAAC TACTTCATCA    3420
AAAACATGG  AAATGGTCCA ACAGAAAAAA GAGGGCCCCA TTCCACCAGA TGCACAAAAT    3480
CCAGATATGT CGTTCTTTAA GATGCTATTC TTGCCAGAAT CAGCAAGGTG GATACAAAGG    3540
ACTCATGGAA AGAACTCTCT GAACTCTGGG CAAGGCCCCA GTCCAAAGCA ATTAGTATCC    3600
TTAGGACCAG AAAAATCTGT GGAAGGTCAG AATTTCTTGT CTGAGAAAAA CAAAGTGGTA    3660
GTAGGAAAGG GTGAATTTAC AAAGGACGTA GGACTCAAAG AGATGGTTTT TCCAAGCAGC    3720
AGAAACCTAT TTCTTACTAA CTTGGATAAT TTACATGAAA ATAATACACA CAATCAAGAA    3780
AAAAAAATTC AGGAAGAAAT AGAAAAGAAG GAAACATTAA TCCAAGAGAA TGTAGTTTTG    3840
CCTCAGATAC ATACAGTGAC TGGCACTAAG AATTTCATGA AGAACCTTTT CTTACTGAGC    3900
ACTAGGCAAA ATGTAGAAGG TTCATATGAG GGGGCATATG CTCCAGTACT TCAAGATTTT    3960
AGGTCATTAA ATGATTCAAC AAATAGAACA AAGAAACACA CAGCTCATTT CTCAAAAAAA    4020
GGGGAGGAAG AAAACTTGGA AGGCTTGGGA AATCAAACCA AGCAAATTGT AGAGAAATAT    4080
GCATGCACCA CAAGGATATC TCCTAATACA AGCCAGCAGA ATTTTGTCAC GCAACGTAGT    4140
AAGAGAGCTT TGAAACAATT CAGACTCCCA CTAGAAGAAA CAGAACTTGA AAAAAGGATA    4200
ATTGTGGATG ACACCTCAAC CCAGTGGTCC AAAAACATGA ACATTTGAC  CCCGAGCACC    4260
CTCACACAGA TAGACTACAA TGAGAAGGAG AAAGGGGCCA TTACTCAGTC TCCCTTATCA    4320
GATTGCCTTA CGAGGAGTCA TAGCATCCCT CAAGCAAATA GATCTCCATT ACCCATTGCA    4380
AAGGTATCAT CATTTCCATC TATTAGACCT ATATATCTGA CCAGGGTCCT ATTCCAAGAC    4440
AACTCTTCTC ATCTTCCAGC AGCATCTTAT AGAAAGAAAG ATTCTGGGGT CCAAGAAAGC    4500
AGTCATTTCT TACAAGGAGC CAAAAAAAAT AACCTTTCTT TAGCCATTCT AACCTTGGAG    4560
ATGACTGGTG ATCAAAGAGA GGTTGGCTCC CTGGGGACAA GTGCCACAAA TTCAGTCACA    4620
TACAAGAAAG TTGAGAACAC TGTTCTCCCG AAACCAGACT TGCCCAAAAC ATCTGGCAAA    4680
GTTGAATTGC TTCCAAAAGT TCACATTTAT CAGAAGGACC TATTCCCTAC GGAAACTAGC    4740
AATGGGTCTC CTGGCCATCT GGATCTCGTG AAGGGAGCC  TTCTTCAGGG AACAGAGGGA    4800
GCGATTAAGT GGAATGAAGC AAACAGACCT GGAAAAGTTC CCTTTCTGAG AGTAGCAACA    4860
GAAAGCTCTG CAAAGACTCC CTCCAAGCTA TTGGATCCTC TTGCTTGGGA TAACCACTAT    4920
GGTACTCAGA TACCAAAAGA AGAGTGGAAA TCCCAAGAGA AGTCACCAGA AAAAACAGCT    4980
TTTAAGAAAA AGGATACCAT TTTGTCCCTG AACGCTTGTG AAAGCAATCA TGCAATAGCA    5040
GCAATAAATG AGGGACAAAA TAAGCCCGAA ATAGAAGTCA CCTGGGCAAA GCAAGGTAGG    5100
ACTGAAAGGC TGTGCTCTCA AAACCCACCA GTCTTGAAAC GCCATCAACG GGAAATAACT    5160
CGTACTACTC TTCAGTCAGA TCAAGAGGAA ATTGACTATG ATGATACCAT ATCAGTTGAA    5220
ATGAAGAAGG AAGATTTTGA CATTTATGAT GAGGATGAAA ATCAGAGCCC CCGCAGCTTT    5280
```

```
CAAAAGAAAA CACGACACTA TTTTATTGCT GCAGTGGAGA GGCTCTGGGA TTATGGGATG    5340
AGTAGCTCCC CACATGTTCT AAGAAACAGG GCTCAGAGTG GCAGTGTCCC TCAGTTCAAG    5400
AAAGTTGTTT TCCAGGAATT TACTGATGGC TCCTTTACTC AGCCCTTATA CCGTGGAGAA    5460
CTAAATGAAC ATTTGGGACT CCTGGGGCCA TATATAAGAG CAGAAGTTGA AGATAATATC    5520
ATGGTAACTT TCAGAAATCA GGCCTCTCGT CCCTATTCCT TCTATTCTAG CCTTATTTCT    5580
TATGAGGAAG ATCAGAGGCA AGGAGCAGAA CCTAGAAAAA ACTTTGTCAA GCCTAATGAA    5640
ACCAAAACTT ACTTTTGGAA AGTGCAACAT CATATGGCAC CCACTAAAGA TGAGTTTGAC    5700
TGCAAAGCCT GGGCTTATTT CTCTGATGTT GACCTGGAAA AAGATGTGCA CTCAGGCCTG    5760
ATTGGACCCC TTCTGGTCTG CCACACTAAC ACACTGAACC CTGCTCATGG GAGACAAGTG    5820
ACAGTACAGG AATTTGCTCT GTTTTCACC ATCTTTGATG AGACCAAAAG CTGGTACTTC    5880
ACTGAAAATA TGGAAAGAAA CTGCAGGGCT CCCTGCAATA TCCAGATGGA AGATCCCACT    5940
TTTAAAGAGA ATTATCGCTT CCATGCAATC AATGGCTACA TAATGGATAC ACTACCTGGC    6000
TTAGTAATGG CTCAGGATCA AAGGATTCGA TGGTATCTGC TCAGCATGGG CAGCAATGAA    6060
AACATCCATT CTATTCATTT CAGTGGACAT GTGTTCACTG TACGAAAAAA AGAGGAGTAT    6120
AAAATGGCAC TGTACAATCT CTATCCAGGT GTTTTTGAGA CAGTGGAAAT GTTACCATCC    6180
AAAGCTGGAA TTTGGCGGGT GGAATGCCTT ATTGGCGAGC ATCTACATGC TGGGATGAGC    6240
ACACTTTTTC TGGTGTACAG CAATAAGTGT CAGACTCCCC TGGGAATGGC TTCTGGACAC    6300
ATTAGAGATT TTCAGATTAC AGCTTCAGGA CAATATGGAC AGTGGGCCCC AAAGCTGGCC    6360
AGACTTCATT ATTCCGGATC AATCAATGCC TGGAGCACCA AGGAGCCCTT TCTTGGATC    6420
AAGGTGGATC TGTTGGCACC AATGATTATT CACGGCATCA AGACCCAGGG TGCCCGTCAG    6480
AAGTTCTCCA GCCTCTACAT CTCTCAGTTT ATCATCATGT ATAGTCTTGA TGGGAAGAAG    6540
TGGCAGACTT ATCGAGGAAA TTCCACTGGA ACCTTAATGG TCTTCTTTGG CAATGTGGAT    6600
TCATCTGGGA TAAAACACAA TATTTTTAAC CCTCCAATTA TTGCTCGATA CATCCGTTTG    6660
CACCCAACTC ATTATAGCAT TCGCAGCACT CTTCGCATGG AGTTGATGGG CTGTGATTTA    6720
AATAGTTGCA GCATGCCATT GGGAATGGAG AGTAAAGCAA TATCAGATGC ACAGATTACT    6780
GCTTCATCCT ACTTTACCAA TATGTTTGCC ACCTGGTCTC CTTCAAAAGC TCGACTTCAC    6840
CTCCAAGGGA GGAGTAATGC CTGGAGACCT CAGGTGAATA ATCCAAAAGA GTGGCTGCAA    6900
GTGGACTTCC AGAAGACAAT GAAAGTCACA GGAGTAACTA CTCAGGGAGT AAAATCTCTG    6960
CTTACCAGCA TGTATGTGAA GGAGTTCCTC ATCTCCAGCA GTCAAGATGG CCATCAGTGG    7020
ACTCTCTTTT TTCAGAATGG CAAAGTAAAG GTTTTTCAGG GAAATCAAGA CTCCTTCACA    7080
CCTGTGGTGA ACTCTCTAGA CCCACCGTTA CTGACTCGCT ACCTTCGAAT TCACCCCCAG    7140
AGTTGGGTGC ACCAGATTGC CCTGAGGATG GAGGTTCTGG GCTGCGAGGC ACAGGACCTC    7200
TACTGAGGGT GGCCACTGCA GCACCTGCCA CTGCCGTCAC CTCTCCCTCC TCAGCTCCAG    7260
GGCAGTGTCC CTCCCTGGCT TGCCTTCTAC CTTTGTGCTA AATCCTAGCA GACACTGCCT    7320
TGAAGCCTCC TGAATTAACT ATCATCAGTC CTGCATTTCT TTGGTGGGGG GCCAGGAGGG    7380
TGCATCCAAT TTAACTTAAC TCTTACCTAT TTTCTGCAGC TGCTCCCAGA TTACTCCTTC    7440
CTTCCAATAT AACTAGGCAA AAAGAAGTGA GGAGAAACCT GCATGAAAGC ATTCTTCCCT    7500
GAAAAGTTAG GCCTCTCAGA GTCACCACTT CCTCTGTTGT AGAAAAACTA TGTGATGAAA    7560
CTTTGAAAAA GATATTTATG ATGTTAACAT TCAGGTTAAA GCCTCATACG TTTAAAATAA    7620
AACTCTCAGT TGTTTATTAT CCTGATCAAG CATGGAACAA AGCATGTTTC AGGATCAGAT    7680
CAATACAATC TTGGAGTCAA AAGGCAAATC ATTTGGACAA TCTGCAAAAT GGAGAGAATA    7740
```

| | | | | | |
|---|---|---|---|---|---|
| CAATAACTAC | TACAGTAAAG | TCTGTTTCTG | CTTCCTTACA | CATAGATATA | ATTATGTTAT | 7800 |
| TTAGTCATTA | TGAGGGGCAC | ATTCTTATCT | CCAAAACTAG | CATTCTTAAA | CTGAGAATTA | 7860 |
| TAGATGGGGT | TCAAGAATCC | CTAAGTCCCC | TGAAATTATA | TAAGGCATTC | TGTATAAATG | 7920 |
| CAAATGTGCA | TTTTTCTGAC | GAGTGTCCAT | AGATATAAAG | CCATTGGTCT | TAATTCTGAC | 7980 |
| CAATAAAAAA | ATAAGTCAGG | AGGATGCAAT | TGTTGAAAGC | TTTGAAATAA | AATAACATGT | 8040 |
| CTTCTTGAAA | TTTGTGATGG | CCAAGAAAGA | AAATGATGAT | GACATTAGGC | TTCTAAAGGA | 8100 |
| CATACATTTA | ATATTTCTGT | GGAAATATGA | GGAAATCCA | TGGTTATCTG | AGATAGGAGA | 8160 |
| TACAAACTTT | GTAATTCTAA | TAATGCACTC | AGTTACTCT | CTCCCTCTAC | TAATTTCCTG | 8220 |
| CTGAAAATAA | CACAACAAAA | ATGTAACAGG | GGAAATTATA | TACCGTGACT | GAAAACTAGA | 8280 |
| GTCCTACTTA | CATAGTTGAA | ATATCAAGGA | GGTCAGAAGA | AAATTGGACT | GGTGAAAACA | 8340 |
| GAAAAAACAC | TCCAGTCTGC | CATATCACCA | CACAATAGGA | TCCCCCTTCT | TGCCCTCCAC | 8400 |
| CCCCATAAGA | TTGTGAAGGG | TTTACTGCTC | CTTCCATCTG | CCTGCACCCC | TTCACTATGA | 8460 |
| CTACACAGAA | CTCTCCTGAT | AGTAAAGGGG | GCTGGAGGCA | AGGATAAGTT | ATAGAGCAGT | 8520 |
| TGGAGGAAGC | ATCCAAAGAC | TGCAACCCAG | GGCAAATGGA | AAACAGGAGA | TCCTAATATG | 8580 |
| AAAGAAAAAT | GGATCCCAAT | CTGAGAAAAG | GCAAAGAAT | GGCTACTTTT | TTCTATGCTG | 8640 |
| GAGTATTTTC | TAATAATCCT | GCTTGACCCT | TATCTGACCT | CTTTGGAAAC | TATAACATAG | 8700 |
| CTGTCACAGT | ATAGTCACAA | TCCACAAATG | ATGCAGGTGC | AAATGGTTTA | TAGCCCTGTG | 8760 |
| AAGTTCTTAA | AGTTTAGAGG | CTAACTTACA | GAAATGAATA | AGTTGTTTTG | TTTTATAGCC | 8820 |
| CGGTAGAGGA | GTTAACCCCA | AAGGTGATAT | GGTTTTATTT | CCTGTTATGT | TTAACTTGAT | 8880 |
| AATCTTATTT | TGGCATTCTT | TTCCCATTGA | CTATATACAT | CTCTATTTCT | CAAATGTTCA | 8940 |
| TGGAACTAGC | TCTTTTATTT | TCCTGCTGGT | TTCTTCAGTA | ATGAGTTAAA | TAAAACATTG | 9000 |
| ACACATACA | | | | | | 9009 |

( 2 ) INFORMATION FOR SEQ ID NO:4:

( i ) SEQUENCE CHARACTERISTICS:
        ( A ) LENGTH: 2332 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapien
        ( F ) TISSUE TYPE: Liver cDNA sequence ( x i ) SEQUENCE DESCRIPTION: SEQ ID NO:4:

```
Ala  Thr  Arg  Arg  Tyr  Tyr  Leu  Gly  Ala  Val  Glu  Leu  Ser  Trp  Asp  Tyr
 1                 5                           10                          15

Met  Gln  Ser  Asp  Leu  Gly  Glu  Leu  Pro  Val  Asp  Ala  Arg  Phe  Pro  Pro
               20                          25                          30

Arg  Val  Pro  Lys  Ser  Phe  Pro  Phe  Asn  Thr  Ser  Val  Val  Tyr  Lys  Lys
          35                          40                          45

Thr  Leu  Phe  Val  Glu  Phe  Thr  Val  His  Leu  Phe  Asn  Ile  Ala  Lys  Pro
     50                          55                          60

Arg  Pro  Pro  Trp  Met  Gly  Leu  Leu  Gly  Pro  Thr  Ile  Gln  Ala  Glu  Val
65                      70                          75                          80
```

| | | | | | | | | | | | | | | |
|---|---|---|---|---|---|---|---|---|---|---|---|---|---|---|
| Tyr | Asp | Thr | Val | Val | Ile | Thr | Leu | Lys | Asn | Met | Ala | Ser | His | Pro | Val |
| | | | 85 | | | | | 90 | | | | 95 | |
| Ser | Leu | His | Ala | Val | Gly | Val | Ser | Tyr | Trp | Lys | Ala | Ser | Glu | Gly | Ala |
| | | | 100 | | | | | 105 | | | | | 110 | | |
| Glu | Tyr | Asp | Asp | Gln | Thr | Ser | Gln | Arg | Glu | Lys | Glu | Asp | Asp | Lys | Val |
| | | | 115 | | | | | 120 | | | | | 125 | | |
| Phe | Pro | Gly | Gly | Ser | His | Thr | Tyr | Val | Trp | Gln | Val | Leu | Lys | Glu | Asn |
| | 130 | | | | | 135 | | | | | 140 | | | | |
| Gly | Pro | Met | Ala | Ser | Asp | Pro | Leu | Cys | Leu | Thr | Tyr | Ser | Tyr | Leu | Ser |
| 145 | | | | | 150 | | | | | 155 | | | | | 160 |
| His | Val | Asp | Leu | Val | Lys | Asp | Leu | Asn | Ser | Gly | Leu | Ile | Gly | Ala | Leu |
| | | | | 165 | | | | | 170 | | | | | 175 | |
| Leu | Val | Cys | Arg | Glu | Gly | Ser | Leu | Ala | Lys | Glu | Lys | Thr | Gln | Thr | Leu |
| | | | 180 | | | | | 185 | | | | | 190 | | |
| His | Lys | Phe | Ile | Leu | Leu | Phe | Ala | Val | Phe | Asp | Glu | Gly | Lys | Ser | Trp |
| | | | 195 | | | | | 200 | | | | | 205 | | |
| His | Ser | Glu | Thr | Lys | Asn | Ser | Leu | Met | Gln | Asp | Arg | Asp | Ala | Ala | Ser |
| | | | 210 | | | | | 215 | | | | | 220 | | |
| Ala | Arg | Ala | Trp | Pro | Lys | Met | His | Thr | Val | Asn | Gly | Tyr | Val | Asn | Arg |
| 225 | | | | | 230 | | | | | 235 | | | | | 240 |
| Ser | Leu | Pro | Gly | Leu | Ile | Gly | Cys | His | Arg | Lys | Ser | Val | Tyr | Trp | His |
| | | | | 245 | | | | | 250 | | | | | 255 | |
| Val | Ile | Gly | Met | Gly | Thr | Thr | Pro | Glu | Val | His | Ser | Ile | Phe | Leu | Glu |
| | | | 260 | | | | | 265 | | | | | 270 | | |
| Gly | His | Thr | Phe | Leu | Val | Arg | Asn | His | Arg | Gln | Ala | Ser | Leu | Glu | Ile |
| | | | 275 | | | | | 280 | | | | | 285 | | |
| Ser | Pro | Ile | Thr | Phe | Leu | Thr | Ala | Gln | Thr | Leu | Leu | Met | Asp | Leu | Gly |
| | 290 | | | | | 295 | | | | | 300 | | | | |
| Gln | Phe | Leu | Leu | Phe | Cys | His | Ile | Ser | Ser | His | Gln | His | Asp | Gly | Met |
| 305 | | | | | 310 | | | | | 315 | | | | | 320 |
| Glu | Ala | Tyr | Val | Lys | Val | Asp | Ser | Cys | Pro | Glu | Glu | Pro | Gln | Leu | Arg |
| | | | | 325 | | | | | 330 | | | | | 335 | |
| Met | Lys | Asn | Asn | Glu | Glu | Ala | Glu | Asp | Tyr | Asp | Asp | Asp | Leu | Thr | Asp |
| | | | 340 | | | | | 345 | | | | | 350 | | |
| Ser | Glu | Met | Asp | Val | Val | Arg | Phe | Asp | Asp | Asp | Asn | Ser | Pro | Ser | Phe |
| | | | 355 | | | | | 360 | | | | | 365 | | |
| Ile | Gln | Ile | Arg | Ser | Val | Ala | Lys | Lys | His | Pro | Lys | Thr | Trp | Val | His |
| | 370 | | | | | 375 | | | | | 380 | | | | |
| Tyr | Ile | Ala | Ala | Glu | Glu | Glu | Asp | Trp | Asp | Tyr | Ala | Pro | Leu | Val | Leu |
| 385 | | | | | 390 | | | | | 395 | | | | | 400 |
| Ala | Pro | Asp | Asp | Arg | Ser | Tyr | Lys | Ser | Gln | Tyr | Leu | Asn | Asn | Gly | Pro |
| | | | | 405 | | | | | 410 | | | | | 415 | |
| Gln | Arg | Ile | Gly | Arg | Lys | Tyr | Lys | Lys | Val | Arg | Phe | Met | Ala | Tyr | Thr |
| | | | 420 | | | | | 425 | | | | | 430 | | |
| Asp | Glu | Thr | Phe | Lys | Thr | Arg | Glu | Ala | Ile | Gln | His | Glu | Ser | Gly | Ile |
| | | | 435 | | | | | 440 | | | | | 445 | | |
| Leu | Gly | Pro | Leu | Leu | Tyr | Gly | Glu | Val | Gly | Asp | Thr | Leu | Leu | Ile | Ile |
| | 450 | | | | | 455 | | | | | 460 | | | | |
| Phe | Lys | Asn | Gln | Ala | Ser | Arg | Pro | Tyr | Asn | Ile | Tyr | Pro | His | Gly | Ile |
| 465 | | | | | 470 | | | | | 475 | | | | | 480 |
| Thr | Asp | Val | Arg | Pro | Leu | Tyr | Ser | Arg | Arg | Leu | Pro | Lys | Gly | Val | Lys |
| | | | | 485 | | | | | 490 | | | | | 495 | |
| His | Leu | Lys | Asp | Phe | Pro | Ile | Leu | Pro | Gly | Glu | Ile | Phe | Lys | Tyr | Lys |
| | | | 500 | | | | | 505 | | | | | 510 | | |

| | | | | | | | | | | | | | | |
|---|---|---|---|---|---|---|---|---|---|---|---|---|---|---|
|Trp|Thr|Val 515|Thr|Val|Glu|Asp|Gly 520|Pro|Thr|Lys|Ser 525|Asp|Pro|Arg|Cys|
|Leu|Thr 530|Arg|Tyr|Tyr|Ser|Ser 535|Phe|Val|Asn|Met|Glu 540|Arg|Asp|Leu|Ala|
|Ser 545|Gly|Leu|Ile|Gly|Pro 550|Leu|Leu|Ile|Cys|Tyr 555|Lys|Glu|Ser|Val|Asp 560|
|Gln|Arg|Gly|Asn|Gln 565|Ile|Met|Ser|Asp|Lys 570|Arg|Asn|Val|Ile|Leu 575|Phe|
|Ser|Val|Phe|Asp 580|Glu|Asn|Arg|Ser|Trp 585|Tyr|Leu|Thr|Glu|Asn 590|Ile|Gln|
|Arg|Phe|Leu 595|Pro|Asn|Pro|Ala|Gly 600|Val|Gln|Leu|Glu|Asp 605|Pro|Glu|Phe|
|Gln|Ala|Ser 610|Asn|Ile|Met|His 615|Ser|Ile|Asn|Gly|Tyr 620|Val|Phe|Asp|Ser|
|Leu 625|Gln|Leu|Ser|Val|Cys 630|Leu|His|Glu|Val|Ala 635|Tyr|Trp|Tyr|Ile|Leu 640|
|Ser|Ile|Gly|Ala|Gln 645|Thr|Asp|Phe|Leu|Ser 650|Val|Phe|Phe|Ser|Gly 655|Tyr|
|Thr|Phe|Lys|His 660|Lys|Met|Val|Tyr|Glu 665|Asp|Thr|Leu|Thr|Leu 670|Phe|Pro|
|Phe|Ser|Gly 675|Glu|Thr|Val|Phe|Met 680|Ser|Met|Glu|Asn|Pro 685|Gly|Leu|Trp|
|Ile|Leu|Gly 690|Cys|His|Asn|Ser|Asp 695|Phe|Arg|Asn|Arg|Gly 700|Met|Thr|Ala|
|Leu 705|Leu|Lys|Val|Ser|Ser 710|Cys|Asp|Lys|Asn|Thr 715|Gly|Asp|Tyr|Tyr|Glu 720|
|Asp|Ser|Tyr|Glu|Asp 725|Ile|Ser|Ala|Tyr|Leu 730|Leu|Ser|Lys|Asn|Asn 735|Ala|
|Ile|Glu|Pro|Arg 740|Ser|Phe|Ser|Gln|Asn 745|Ser|Arg|His|Pro|Ser 750|Thr|Arg|
|Gln|Lys|Gln 755|Phe|Asn|Ala|Thr|Thr 760|Ile|Pro|Glu|Asn|Asp 765|Ile|Glu|Lys|
|Thr|Asp 770|Pro|Trp|Phe|Ala|His 775|Arg|Thr|Pro|Met|Pro 780|Lys|Ile|Gln|Asn|
|Val 785|Ser|Ser|Ser|Asp|Leu 790|Leu|Met|Leu|Leu|Arg 795|Gln|Ser|Pro|Thr|Pro 800|
|His|Gly|Leu|Ser|Leu 805|Ser|Asp|Leu|Gln|Glu 810|Ala|Lys|Tyr|Glu|Thr 815|Phe|
|Ser|Asp|Asp|Pro 820|Ser|Pro|Gly|Ala|Ile 825|Asp|Ser|Asn|Asn|Ser 830|Leu|Ser|
|Glu|Met|Thr 835|His|Phe|Arg|Pro|Gln 840|Leu|His|His|Ser|Gly 845|Asp|Met|Val|
|Phe|Thr|Pro 850|Glu|Ser|Gly|Leu|Gln 855|Leu|Arg|Leu|Asn|Glu 860|Lys|Leu|Gly|
|Thr 865|Thr|Ala|Ala|Thr|Glu 870|Leu|Lys|Lys|Leu|Asp 875|Phe|Lys|Val|Ser|Ser 880|
|Thr|Ser|Asn|Asn|Leu 885|Ile|Ser|Thr|Ile|Pro 890|Ser|Asp|Asn|Leu|Ala 895|Ala|
|Gly|Thr|Asp|Asn 900|Thr|Ser|Ser|Leu|Gly 905|Pro|Pro|Ser|Met|Pro 910|Val|His|
|Tyr|Asp|Ser 915|Gln|Leu|Asp|Thr|Thr 920|Leu|Phe|Gly|Lys|Lys 925|Ser|Ser|Pro|
|Leu|Thr|Glu 930|Ser|Gly|Gly|Pro|Leu 935|Ser|Leu|Ser|Glu|Glu 940|Asn|Asn|Asp|
|Ser|Lys|Leu|Leu|Glu|Ser|Gly|Leu|Met|Asn|Ser|Gln|Glu|Ser|Ser|Trp|

-continued

```
945                      950                      955                      960

Gly  Lys  Asn  Val  Ser  Ser  Thr  Glu  Ser  Gly  Arg  Leu  Phe  Lys  Gly  Lys
                    965                      970                      975

Arg  Ala  His  Gly  Pro  Ala  Leu  Leu  Thr  Lys  Asp  Asn  Ala  Leu  Phe  Lys
                    980                      985                      990

Val  Ser  Ile  Ser  Leu  Leu  Lys  Thr  Asn  Lys  Thr  Ser  Asn  Asn  Ser  Ala
                    995                      1000                     1005

Thr  Asn  Arg  Lys  Thr  His  Ile  Asp  Gly  Pro  Ser  Leu  Leu  Ile  Glu  Asn
                    1010                     1015                     1020

Ser  Pro  Ser  Val  Trp  Gln  Asn  Ile  Leu  Glu  Ser  Asp  Thr  Glu  Phe  Lys
1025                     1030                     1035                     1040

Lys  Val  Thr  Pro  Leu  Ile  His  Asp  Arg  Met  Leu  Met  Asp  Lys  Asn  Ala
                    1045                     1050                     1055

Thr  Ala  Leu  Arg  Leu  Asn  His  Met  Ser  Asn  Lys  Thr  Thr  Ser  Ser  Lys
                    1060                     1065                     1070

Asn  Met  Glu  Met  Val  Gln  Gln  Lys  Lys  Glu  Gly  Pro  Ile  Pro  Pro  Asp
                    1075                     1080                     1085

Ala  Gln  Asn  Pro  Asp  Met  Ser  Phe  Phe  Lys  Met  Leu  Phe  Leu  Pro  Glu
                    1090                     1095                     1100

Ser  Ala  Arg  Trp  Ile  Gln  Arg  Thr  His  Gly  Lys  Asn  Ser  Leu  Asn  Ser
1105                     1110                     1115                     1120

Gly  Gln  Gly  Pro  Ser  Pro  Lys  Gln  Leu  Val  Ser  Leu  Gly  Pro  Glu  Lys
                    1125                     1130                     1135

Ser  Val  Glu  Gly  Gln  Asn  Phe  Leu  Ser  Glu  Lys  Asn  Lys  Val  Val  Val
                    1140                     1145                     1150

Gly  Lys  Gly  Glu  Phe  Thr  Lys  Asp  Val  Gly  Leu  Lys  Glu  Met  Val  Phe
                    1155                     1160                     1165

Pro  Ser  Ser  Arg  Asn  Leu  Phe  Leu  Thr  Asn  Leu  Asp  Asn  Leu  His  Glu
                    1170                     1175                     1180

Asn  Asn  Thr  His  Asn  Gln  Glu  Lys  Lys  Ile  Gln  Glu  Glu  Ile  Glu  Lys
1185                     1190                     1195                     1200

Lys  Glu  Thr  Leu  Ile  Gln  Glu  Asn  Val  Val  Leu  Pro  Gln  Ile  His  Thr
                    1205                     1210                     1215

Val  Thr  Gly  Thr  Lys  Asn  Phe  Met  Lys  Asn  Leu  Phe  Leu  Leu  Ser  Thr
                    1220                     1225                     1230

Arg  Gln  Asn  Val  Glu  Gly  Ser  Tyr  Glu  Gly  Ala  Tyr  Ala  Pro  Val  Leu
                    1235                     1240                     1245

Gln  Asp  Phe  Arg  Ser  Leu  Asn  Asp  Ser  Thr  Asn  Arg  Thr  Lys  Lys  His
                    1250                     1255                     1260

Thr  Ala  His  Phe  Ser  Lys  Lys  Gly  Glu  Glu  Glu  Asn  Leu  Glu  Gly  Leu
1265                     1270                     1275                     1280

Gly  Asn  Gln  Thr  Lys  Gln  Ile  Val  Glu  Lys  Tyr  Ala  Cys  Thr  Thr  Arg
                    1285                     1290                     1295

Ile  Ser  Pro  Asn  Thr  Ser  Gln  Gln  Asn  Phe  Val  Thr  Gln  Arg  Ser  Lys
                    1300                     1305                     1310

Arg  Ala  Leu  Lys  Gln  Phe  Arg  Leu  Pro  Leu  Glu  Glu  Thr  Glu  Leu  Glu
                    1315                     1320                     1325

Lys  Arg  Ile  Ile  Val  Asp  Asp  Thr  Ser  Thr  Gln  Trp  Ser  Lys  Asn  Met
                    1330                     1335                     1340

Lys  His  Leu  Thr  Pro  Ser  Thr  Leu  Thr  Gln  Ile  Asp  Tyr  Asn  Glu  Lys
                    1345                     1350                     1355                     1360

Glu  Lys  Gly  Ala  Ile  Thr  Gln  Ser  Pro  Leu  Ser  Asp  Cys  Leu  Thr  Arg
                    1365                     1370                     1375

Ser  His  Ser  Ile  Pro  Gln  Ala  Asn  Arg  Ser  Pro  Leu  Pro  Ile  Ala  Lys
                    1380                     1385                     1390
```

```
Val Ser Ser Phe Pro Ser Ile Arg Pro Ile Tyr Leu Thr Arg Val Leu
    1395                1400                1405
Phe Gln Asp Asn Ser Ser His Leu Pro Ala Ala Ser Tyr Arg Lys Lys
    1410                1415                1420
Asp Ser Gly Val Gln Glu Ser Ser His Phe Leu Gln Gly Ala Lys Lys
1425            1430                1435                    1440
Asn Asn Leu Ser Leu Ala Ile Leu Thr Leu Glu Met Thr Gly Asp Gln
            1445                1450                1455
Arg Glu Val Gly Ser Leu Gly Thr Ser Ala Thr Asn Ser Val Thr Tyr
            1460                1465                1470
Lys Lys Val Glu Asn Thr Val Leu Pro Lys Pro Asp Leu Pro Lys Thr
            1475                1480                1485
Ser Gly Lys Val Glu Leu Leu Pro Lys Val His Ile Tyr Gln Lys Asp
            1490                1495                1500
Leu Phe Pro Thr Glu Thr Ser Asn Gly Ser Pro Gly His Leu Asp Leu
1505                1510                1515                1520
Val Glu Gly Ser Leu Leu Gln Gly Thr Glu Gly Ala Ile Lys Trp Asn
            1525                1530                1535
Glu Ala Asn Arg Pro Gly Lys Val Pro Phe Leu Arg Val Ala Thr Glu
            1540                1545                1550
Ser Ser Ala Lys Thr Pro Ser Lys Leu Leu Asp Pro Leu Ala Trp Asp
            1555                1560                1565
Asn His Tyr Gly Thr Gln Ile Pro Lys Glu Glu Trp Lys Ser Gln Glu
            1570                1575                1580
Lys Ser Pro Glu Lys Thr Ala Phe Lys Lys Lys Asp Thr Ile Leu Ser
1585                1590                1595                1600
Leu Asn Ala Cys Glu Ser Asn His Ala Ile Ala Ala Ile Asn Glu Gly
            1605                1610                1615
Gln Asn Lys Pro Glu Ile Glu Val Thr Trp Ala Lys Gln Gly Arg Thr
            1620                1625                1630
Glu Arg Leu Cys Ser Gln Asn Pro Pro Val Leu Lys Arg His Gln Arg
            1635                1640                1645
Glu Ile Thr Arg Thr Thr Leu Gln Ser Asp Gln Glu Glu Ile Asp Tyr
            1650                1655                1660
Asp Asp Thr Ile Ser Val Glu Met Lys Lys Glu Asp Phe Asp Ile Tyr
1665                1670                1675                1680
Asp Glu Asp Glu Asn Gln Ser Pro Arg Ser Phe Gln Lys Lys Thr Arg
            1685                1690                1695
His Tyr Phe Ile Ala Ala Val Glu Arg Leu Trp Asp Tyr Gly Met Ser
            1700                1705                1710
Ser Ser Pro His Val Leu Arg Asn Arg Ala Gln Ser Gly Ser Val Pro
            1715                1720                1725
Gln Phe Lys Lys Val Val Phe Gln Glu Phe Thr Asp Gly Ser Phe Thr
            1730                1735                1740
Gln Pro Leu Tyr Arg Gly Glu Leu Asn Glu His Leu Gly Leu Leu Gly
1745                1750                1755                1760
Pro Tyr Ile Arg Ala Glu Val Glu Asp Asn Ile Met Val Thr Phe Arg
            1765                1770                1775
Asn Gln Ala Ser Arg Pro Tyr Ser Phe Tyr Ser Ser Leu Ile Ser Tyr
            1780                1785                1790
Glu Glu Asp Gln Arg Gln Gly Ala Glu Pro Arg Lys Asn Phe Val Lys
            1795                1800                1805
Pro Asn Glu Thr Lys Thr Tyr Phe Trp Lys Val Gln His His Met Ala
            1810                1815                1820
```

```
Pro Thr Lys Asp Glu Phe Asp Cys Lys Ala Trp Ala Tyr Phe Ser Asp
1825                1830                1835                1840

Val Asp Leu Glu Lys Asp Val His Ser Gly Leu Ile Gly Pro Leu Leu
            1845                1850                1855

Val Cys His Thr Asn Thr Leu Asn Pro Ala His Gly Arg Gln Val Thr
            1860                1865                1870

Val Gln Glu Phe Ala Leu Phe Phe Thr Ile Phe Asp Glu Thr Lys Ser
        1875                1880                1885

Trp Tyr Phe Thr Glu Asn Met Glu Arg Asn Cys Arg Ala Pro Cys Asn
        1890                1895                1900

Ile Gln Met Glu Asp Pro Thr Phe Lys Glu Asn Tyr Arg Phe His Ala
1905                1910                1915                1920

Ile Asn Gly Tyr Ile Met Asp Thr Leu Pro Gly Leu Val Met Ala Gln
                1925                1930                1935

Asp Gln Arg Ile Arg Trp Tyr Leu Leu Ser Met Gly Ser Asn Glu Asn
            1940                1945                1950

Ile His Ser Ile His Phe Ser Gly His Val Phe Thr Val Arg Lys Lys
            1955                1960                1965

Glu Glu Tyr Lys Met Ala Leu Tyr Asn Leu Tyr Pro Gly Val Phe Glu
        1970                1975                1980

Thr Val Glu Met Leu Pro Ser Lys Ala Gly Ile Trp Arg Val Glu Cys
1985                1990                1995                2000

Leu Ile Gly Glu His Leu His Ala Gly Met Ser Thr Leu Phe Leu Val
                2005                2010                2015

Tyr Ser Asn Lys Cys Gln Thr Pro Leu Gly Met Ala Ser Gly His Ile
            2020                2025                2030

Arg Asp Phe Gln Ile Thr Ala Ser Gly Gln Tyr Gly Gln Trp Ala Pro
            2035                2040                2045

Lys Leu Ala Arg Leu His Tyr Ser Gly Ser Ile Asn Ala Trp Ser Thr
2050                2055                2060

Lys Glu Pro Phe Ser Trp Ile Lys Val Asp Leu Leu Ala Pro Met Ile
2065                2070                2075                2080

Ile His Gly Ile Lys Thr Gln Gly Ala Arg Gln Lys Phe Ser Ser Leu
            2085                2090                2095

Tyr Ile Ser Gln Phe Ile Ile Met Tyr Ser Leu Asp Gly Lys Lys Trp
        2100                2105                2110

Gln Thr Tyr Arg Gly Asn Ser Thr Gly Thr Leu Met Val Phe Phe Gly
        2115                2120                2125

Asn Val Asp Ser Ser Gly Ile Lys His Asn Ile Phe Asn Pro Pro Ile
    2130                2135                2140

Ile Ala Arg Tyr Ile Arg Leu His Pro Thr His Tyr Ser Ile Arg Ser
2145                2150                2155                2160

Thr Leu Arg Met Glu Leu Met Gly Cys Asp Leu Asn Ser Cys Ser Met
                2165                2170                2175

Pro Leu Gly Met Glu Ser Lys Ala Ile Ser Asp Ala Gln Ile Thr Ala
            2180                2185                2190

Ser Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val Asn
    2210                2215                2220

Asn Pro Lys Glu Trp Leu Gln Val Asp Phe Gln Lys Thr Met Lys Val
2225                2230                2235                2240

Thr Gly Val Thr Thr Gln Gly Val Lys Ser Leu Leu Thr Ser Met Tyr
            2245                2250                2255

Val Lys Glu Phe Leu Ile Ser Ser Ser Gln Asp Gly His Gln Trp Thr
```

|  | 2260 |  |  |  | 2265 |  |  |  | 2270 |  |  |
|---|---|---|---|---|---|---|---|---|---|---|---|
| Leu | Phe | Phe | Gln | Asn | Gly | Lys | Val | Lys | Val | Phe | Gln | Gly | Asn | Gln | Asp |
|  |  | 2275 |  |  |  |  | 2280 |  |  |  | 2285 |  |  |  |

| Ser | Phe | Thr | Pro | Val | Val | Asn | Ser | Leu | Asp | Pro | Pro | Leu | Leu | Thr | Arg |
|  | 2290 |  |  |  |  | 2295 |  |  |  |  | 2300 |  |  |  |  |

| Tyr | Leu | Arg | Ile | His | Pro | Gln | Ser | Trp | Val | His | Gln | Ile | Ala | Leu | Arg |
| 2305 |  |  |  |  | 2310 |  |  |  |  | 2315 |  |  |  |  | 2320 |

| Met | Glu | Val | Leu | Gly | Cys | Glu | Ala | Gln | Asp | Leu | Tyr |
|  |  |  |  | 2325 |  |  |  |  | 2330 |  |  |

( 2 ) INFORMATION FOR SEQ ID NO:5:

( i ) SEQUENCE CHARACTERISTICS:
    ( A ) LENGTH: 1260 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Porcine ( x i ) SEQUENCE DESCRIPTION: SEQ ID NO:5:

| GAATTCTTCA | CTCAGATTCT | CCTGTTCACA | GTAGAAATTC | AGTATTGTTA | GCACTCTTTT | 60 |
| AGTTACCTGT | ATCCTAAACC | TAAGTCCTGC | TCCCTTATAC | TTACTCATCC | TACAAATTGG | 120 |
| TCAGAGTATG | TGTTTGGCAT | TATGTTATGT | GATTGAATG | CATTATCAGA | TACTACTAGT | 180 |
| CTCATTTACA | AATTAGAAAA | CTGGAGCTCA | GAGAGTTCCT | TGGACTTGCT | TAAAGCAACA | 240 |
| CAGCTGGTAA | ATTGTATAGC | TAGGATTCGA | ACCGAGGCAA | TCGTACTCTA | GAACCCATGC | 300 |
| CACTATGTTG | CATAGCATAA | TAGCCCGCCT | ATATAAACTT | GGCTGAATTA | AGTCACGATC | 360 |
| TATCATCACC | AAAGAGTCCG | TGTGACTAAG | AGTCTCAACT | ATTGTATGTC | AATTATATTT | 420 |
| CTCCATTTTT | ATCCCAATAT | ATATTCATTT | AAATCACAGC | CCTTTCTTGT | GGTCACAAAC | 480 |
| AGGTACACTA | GAGCCATGGT | TGGGCTGCAG | TCCATGGTGT | ACATTTAACC | CAACGACCTC | 540 |
| GATATAATGG | TACCGACTAG | TGTTTTGTTT | TTGTTTTTGT | TTCATTTTTC | TGGGAATAGA | 600 |
| AGAGAACCTC | TAACACAGAT | CTTGCTTGGG | ACCTGGGCTG | TGAGTAACCA | GAGTTTTATT | 660 |
| CTTCCTTATC | TCCAGGTCTC | TGGGTCCTAG | GGTGCCACAA | CTCAGACTTG | CGGAACAGAG | 720 |
| GGATGACAGC | CTTACTGAAG | GTGTATAGTT | GTGACAGGGA | CACTGGTGAT | TATTATGACA | 780 |
| ACACTTATGA | AGATATTCCA | GGCTTCTTGC | TGAGTGGAAA | GAATGTCATT | GAACCCAGAA | 840 |
| GCTTTGCCCA | GAATTCAAGA | CCCCCTAGTG | CGAGCCAAAA | GCAATTCCAA | ACCATCACAA | 900 |
| GTCCAGAAGA | TGACGTGGAG | CTTGACCCGC | AGTCTGGAGA | GAGAACCCAA | GCACTGGAAG | 960 |
| AACTAAGTGT | CCCCTCTGGT | GATGGGTCGA | TGCTCTTGGG | ACAGAATCCT | GCTCCACATG | 1020 |
| GCTCATCCTC | ATCTGATCTT | CAAGAAGCCA | GGAATGAGGC | TGATGATTAT | TTACCTGGAG | 1080 |
| CAAGAGAAAG | AAACACGGCC | CCATCCGCAG | CGGCACGTCT | CAGACCAGAG | CTGCATCACA | 1140 |
| GTGCCGAAAG | AGTACTTACT | CCTGAGCCAG | AGAAAGAGTT | GAAGAAACTT | GATTCTTAAA | 1200 |
| TGTCTAGTTC | ATCAGACCTT | CTAAAGACTT | CGCCAACAAT | TCCATCAGAC | ACGTTGTCAG | 1260 |

( 2 ) INFORMATION FOR SEQ ID NO:6:

( i ) SEQUENCE CHARACTERISTICS:
    ( A ) LENGTH: 868 amino acids
    ( B ) TYPE: amino acid (C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
    (A) ORGANISM: Porcine (xi) SEQUENCE DESCRIPTION: SEQ ID NO:6:

```
Gly Leu Trp Val Leu Gly Cys His Met Ser Asp Leu Arg Asn Arg Gly
 1               5                  10                  15
Met Thr Ala Leu Leu Lys Val Tyr Ser Cys Asp Arg Asp Thr Gly Asp
                20                  25                  30
Tyr Tyr Asp Asn Thr Tyr Glu Asp Leu Pro Gly Phe Leu Leu Ser Gly
            35                  40                  45
Lys Asn Val Ile Glu Pro Arg Ser Phe Ala Gln Asn Ser Arg Pro Pro
 50                  55                  60
Ser Ala Ser Gln Lys Gln Phe Gln Thr Ile Thr Ser Pro Glu Asp Asp
 65                  70                  75                  80
Val Glu Leu Asp Pro Gln Ser Gln Glu Arg Thr Gln Ala Leu Glu Glu
                85                  90                  95
Leu Ser Val Pro Ser Gly Asp Gly Ser Met Leu Leu Gly Gln Asn Pro
               100                 105                 110
Ala Pro His Gly Ser Ser Ser Asp Leu Gln Glu Ala Arg Asn Glu
               115                 120                 125
Ala Asp Asp Tyr Leu Pro Gly Ala Arg Glu Arg Asn Thr Ala Pro Ser
           130                 135                 140
Ala Ala Ala Arg Leu Arg Pro Glu Leu His His Ser Ala Glu Arg Val
145                 150                 155                 160
Leu Thr Pro Glu Pro Glu Lys Glu Leu Lys Lys Leu Asp Ser Lys Met
               165                 170                 175
Ser Ser Ser Ser Asp Leu Leu Lys Thr Ser Pro Thr Ile Pro Ser Asp
           180                 185                 190
Thr Leu Ser Ala Glu Thr Glu Arg Thr His Ser Leu Gly Pro Pro His
       195                 200                 205
Pro Gln Val Asn Phe Arg Ser Gln Leu Gly Ala Ile Val Leu Gly Lys
   210                 215                 220
Asn Ser Ser His Phe Ile Gly Ala Gly Val Pro Leu Gly Ser Thr Glu
225                 230                 235                 240
Phe Asp His Glu Ser Ser Leu Gly Glu Asn Val Ser Pro Val Glu Ser
               245                 250                 255
Asp Gly Ile Phe Glu Lys Glu Arg Ala His Gly Pro Ala Ser Leu Thr
           260                 265                 270
Lys Asp Asp Val Leu Phe Lys Val Asn Ile Ser Leu Val Lys Thr Asn
       275                 280                 285
Lys Ala Arg Val Tyr Leu Lys Thr Asn Arg Lys Ile His Ile Asp Asp
   290                 295                 300
Ala Ala Leu Leu Thr Glu Asn Arg Ala Ser Ala Thr Phe Met Asp Lys
305                 310                 315                 320
Asn Thr Thr Ala Ser Gly Leu Asn His Val Ser Asn Trp Ile Lys Gly
               325                 330                 335
Pro Leu Gly Lys Asn Pro Leu Ser Ser Glu Arg Gly Pro Ser Pro Glu
           340                 345                 350
```

```
Leu Leu Thr Ser Ser Gly Ser Gly Lys Ser Val Lys Gly Gln Ser Ser
        355             360             365
Gly Gln Gly Arg Ile Arg Val Ala Val Glu Glu Glu Leu Ser Lys
370             375             380
Gly Lys Glu Met Met Leu Pro Asn Ser Glu Leu Thr Phe Leu Thr Asn
385             390             395                 400
Ser Ala Asp Val Gln Gly Asn Asp Thr His Ser Gln Gly Lys Lys Ser
                405             410             415
Arg Glu Glu Met Glu Arg Arg Glu Leu Val Gln Glu Lys Val Asp Leu
            420             425             430
Pro Gln Val Tyr Thr Ala Thr Gly Thr Lys Asn Phe Leu Arg Asn Ile
        435             440             445
Phe His Gln Ser Thr Glu Pro Ser Val Glu Gly Phe Asp Gly Gly Ser
    450             455             460
His Ala Pro Val Pro Gln Asp Ser Arg Ser Leu Asn Asp Ser Ala Glu
465             470             475             480
Arg Ala Glu Thr His Ile Ala His Phe Ser Ala Ile Arg Glu Glu Ala
            485             490             495
Pro Leu Glu Ala Pro Gly Asn Phe Thr Gly Pro Gly Pro Arg Ser Ala
        500             505             510
Val Pro Arg Arg Val Lys Gln Ser Leu Lys Gln Ile Arg Leu Pro Leu
    515             520             525
Glu Glu Ile Lys Pro Glu Arg Gly Val Val Leu Asn Ala Thr Ser Thr
530             535             540
Arg Trp Ser Glu Ser Ser Pro Ile Leu Gln Gly Ala Lys Arg Asn Asn
545             550             555             560
Leu Ser Leu Pro Phe Leu Thr Leu Glu Met Ala Gly Gly Gln Gly Lys
            565             570             575
Ile Ser Ala Leu Gly Lys Ser Ala Ala Gly Pro Leu Ala Ser Gly Lys
        580             585             590
Leu Glu Lys Ala Val Leu Ser Ser Ala Gly Leu Ser Glu Ala Ser Gly
    595             600             605
Lys Ala Glu Phe Leu Pro Lys Val Arg Val His Arg Glu Asp Leu Leu
610             615             620
Pro Gln Lys Thr Ser Asn Val Ser Cys Ala His Gly Asp Ile Gly Gln
625             630             635             640
Glu Ile Phe Leu Gln Lys Thr Arg Gly Pro Val Asn Leu Asn Lys Val
            645             650             655
Asn Arg Pro Gly Arg Thr Pro Ser Lys Leu Leu Gly Pro Pro Met Pro
        660             665             670
Lys Glu Trp Glu Ser Leu Glu Lys Ser Pro Lys Ser Thr Ala Leu Arg
    675             680             685
Thr Lys Asp Ile Leu Ser Leu Pro Leu Asp Arg His Glu Ser Asn His
690             695             700
Ser Ile Ala Ala Lys Asn Glu Gly Gln Ala Phe Thr Gln Arg Glu Ala
705             710             715             720
Ala Trp Thr Lys Gln Gly Gly Pro Gly Arg Leu Cys Ala Pro Lys Pro
            725             730             735
Pro Val Leu Arg Arg His Gln Arg Asp Ile Ser Leu Pro Thr Pro Gln
        740             745             750
Pro Glu Glu Asp Lys Met Asp Tyr Asp Asp Ile Phe Ser Thr Glu Thr
    755             760             765
Lys Gly Glu Asp Phe Asp Ile Tyr Gly Glu Asp Glu Asn Gln Asp Pro
770             775             780
Arg Ser Phe Gln Lys Arg Thr Arg His Tyr Phe Ile Ala Ala Val Glu
```

| 785 | | | | | 790 | | | | | 795 | | | | 800 |
|---|---|---|---|---|---|---|---|---|---|---|---|---|---|---|
| Gln | Leu | Trp | Asp | Tyr 805 | Gly | Met | Ser | Glu | Ser 810 | Pro | Arg | Ala | Leu | Arg 815 | Asn |
| Arg | Ala | Gln | Asn 820 | Gly | Glu | Val | Pro | Arg 825 | Phe | Lys | Lys | Val | Val 830 | Phe | Arg |
| Glu | Phe | Ala 835 | Asp | Gly | Ser | Phe | Thr 840 | Asn | Pro | Ser | Tyr | Arg 845 | Gly | Glu | Leu |
| Asn | Lys 850 | His | Leu | Gly | Leu | Leu 855 | Gly | Pro | Tyr | Ile | Arg 860 | Ala | Glu | Val | Glu |
| Asp 865 | Asn | Ile | Met | | | | | | | | | | | | |